US008541026B2

(12) United States Patent
Qiu et al.

(10) Patent No.: US 8,541,026 B2
(45) Date of Patent: Sep. 24, 2013

(54) SUSTAINED RELEASE FORMULATIONS OF OPIOID AND NONOPIOID ANALGESICS

(75) Inventors: Yihong Qiu, Vernon Hills, IL (US); Cheri E Klein, Northbrook, IL (US)

(73) Assignee: AbbVie Inc., North Chicago, IL (US)

( * ) Notice: Subject to any disclaimer, the term of this patent is extended or adjusted under 35 U.S.C. 154(b) by 1219 days.

(21) Appl. No.: 11/737,914

(22) Filed: Apr. 20, 2007

(65) Prior Publication Data
US 2007/0281018 A1 Dec. 6, 2007

Related U.S. Application Data

(63) Continuation-in-part of application No. 10/949,141, filed on Sep. 24, 2004, now abandoned.

(51) Int. Cl.
*A61K 31/485* (2006.01)
*A61K 9/22* (2006.01)

(52) U.S. Cl.
USPC .......................................... 424/468; 514/282

(58) Field of Classification Search
None
See application file for complete search history.

(56) References Cited

U.S. PATENT DOCUMENTS

| | | |
|---|---|---|
| 2,799,241 A | 7/1957 | Wurster |
| 3,133,132 A | 5/1964 | Loeb et al. |
| 3,173,876 A | 3/1965 | Zobrist |
| 3,276,586 A | 10/1966 | Rosaen |
| 3,480,616 A | 11/1969 | Osipow et al. |
| 3,541,005 A | 11/1970 | Strathmann et al. |
| 3,541,006 A | 11/1970 | Bixler et al. |
| 3,546,142 A | 12/1970 | Michaels et al. |
| 3,845,770 A | 11/1974 | Theeuwes et al. |
| 3,865,108 A | 2/1975 | Hartop |
| 3,916,899 A | 11/1975 | Theeuwes et al. |
| 3,995,631 A | 12/1976 | Higuchi et al. |
| 4,002,173 A | 1/1977 | Manning et al. |
| 4,008,719 A | 2/1977 | Theeuwes et al. |
| 4,034,756 A | 7/1977 | Higuchi et al. |
| 4,063,064 A | 12/1977 | Saunders et al. |
| 4,077,407 A | 3/1978 | Theeuwes et al. |
| 4,088,864 A | 5/1978 | Theeuwes et al. |
| 4,111,201 A | 9/1978 | Theeuwes |
| 4,111,202 A | 9/1978 | Theeuwes |
| 4,160,020 A | 7/1979 | Ayer et al. |
| 4,200,098 A | 4/1980 | Ayer et al. |
| 4,207,893 A | 6/1980 | Michaels |
| 4,235,236 A | 11/1980 | Theeuwes |
| 4,278,087 A | 7/1981 | Theeuwes |
| 4,285,987 A | 8/1981 | Ayer et al. |
| 4,320,759 A | 3/1982 | Theeuwes |
| 4,327,725 A | 5/1982 | Cortese et al. |
| 4,449,983 A | 5/1984 | Cortese et al. |
| 4,464,378 A | 8/1984 | Hussain |
| 4,519,801 A | 5/1985 | Edgren |
| 4,576,604 A | 3/1986 | Guittard et al. |
| 4,578,075 A | 3/1986 | Urquhart et al. |
| 4,612,008 A | 9/1986 | Wong et al. |
| 4,663,149 A | 5/1987 | Eckenhoff et al. |
| 4,681,583 A | 7/1987 | Urquhart et al. |
| 4,717,569 A | 1/1988 | Harrison et al. |
| 4,763,405 A | 8/1988 | Morita et al. |
| 4,765,989 A | 8/1988 | Wong et al. |
| 4,777,049 A | 10/1988 | Magruder et al. |
| 4,783,337 A | 11/1988 | Wong et al. |
| 4,786,503 A | 11/1988 | Edgren et al. |
| 4,801,461 A | 1/1989 | Hamel et al. |
| 4,806,359 A | 2/1989 | Radebaugh et al. |
| 4,816,470 A | 3/1989 | Dowle et al. |
| 4,820,522 A | 4/1989 | Radebaugh et al. |
| 4,844,907 A | 7/1989 | Elger et al. |
| 4,847,077 A | 7/1989 | Raghunathan |
| 4,892,778 A | 1/1990 | Theeuwes et al. |
| 4,915,949 A | 4/1990 | Wong et al. |
| 4,915,954 A | 4/1990 | Ayer et al. |
| 4,931,285 A | 6/1990 | Edgren et al. |
| 4,940,465 A | 7/1990 | Theeuwes et al. |
| 4,946,685 A | 8/1990 | Edgren et al. |
| 4,961,932 A | 10/1990 | Theeuwes |
| 4,968,509 A | 11/1990 | Radebaugh et al. |
| 5,004,613 A | 4/1991 | Radebaugh et al. |
| 5,006,346 A | 4/1991 | Edgren et al. |
| 5,019,397 A | 5/1991 | Wong et al. |
| 5,021,053 A | 6/1991 | Barclay et al. |
| 5,023,088 A | 6/1991 | Wong et al. |
| 5,024,842 A | 6/1991 | Edgren et al. |
| 5,030,456 A | 7/1991 | Ayer et al. |

(Continued)

FOREIGN PATENT DOCUMENTS

| | | |
|---|---|---|
| EP | 0005129 B1 | 4/1981 |
| EP | 220805 A2 | 5/1987 |

(Continued)

OTHER PUBLICATIONS

Barkin, R., "Acetaminophen, Aspirin, or Ibuprofen in Combination Analgesic Products," American Journal of Therapeutics, 2001, vol. 8 (6), pp. 433-442.

BASF, "Lutrol L and Lutrol F—Grades," Pharma Ingredients and Services, Apr. 3, 2010.

BASF, "Pluronic Block Poloxamer NF Grades," 2004.

BASF, "Product Information the Chemical Catalog—Tetronic," 2001.

Cao, et al., "Formulation, Release Characteristics and Bioavailability of Novel Monolithic Hydroxypropylmethylcellulose Matrix Tablets Containing Acetaminophen," Journal of Controlled Release, 2005, vol. 108 (2-3), pp. 351-361.

(Continued)

*Primary Examiner* — Suzanne Ziska
(74) *Attorney, Agent, or Firm* — Lisa V. Mueller; Michael Best & Friedrich LLP

(57) ABSTRACT

The present invention relates to SRSR solid dosage forms for administering pharmaceutical agents, particularly Hydrocodone and acetaminophen, methods for preparing the dosage forms, and methods for providing therapeutic agents to patients in need of treatment.

23 Claims, 7 Drawing Sheets

(56) References Cited

U.S. PATENT DOCUMENTS

| | | |
|---|---|---|
| 5,126,142 A | 6/1992 | Ayer et al. |
| 5,156,850 A | 10/1992 | Wong et al. |
| 5,160,743 A | 11/1992 | Edgren et al. |
| 5,166,145 A | 11/1992 | Jao et al. |
| 5,190,765 A | 3/1993 | Jao et al. |
| 5,200,193 A | 4/1993 | Radebaugh et al. |
| 5,221,536 A | 6/1993 | Edgren et al. |
| 5,252,338 A | 10/1993 | Jao et al. |
| 5,273,760 A | 12/1993 | Oshlack et al. |
| 5,286,493 A | 2/1994 | Oshlack et al. |
| 5,340,590 A | 8/1994 | Wong et al. |
| 5,407,686 A | 4/1995 | Patel et al. |
| 5,417,682 A | 5/1995 | Wong et al. |
| 5,460,826 A | 10/1995 | Merrill et al. |
| 5,512,299 A | 4/1996 | Place et al. |
| 5,529,787 A | 6/1996 | Merrill et al. |
| 5,534,263 A | 7/1996 | Wong et al. |
| 5,593,695 A | 1/1997 | Merrill et al. |
| 5,614,578 A | 3/1997 | Dong et al. |
| 5,620,705 A | 4/1997 | Dong et al. |
| 5,633,011 A | 5/1997 | Dong et al. |
| 5,660,861 A | 8/1997 | Jao et al. |
| 5,667,804 A | 9/1997 | Wong et al. |
| 5,702,725 A | 12/1997 | Merrill et al. |
| 5,830,502 A | 11/1998 | Dong et al. |
| 5,858,407 A | 1/1999 | Ayer et al. |
| 5,866,161 A | 2/1999 | Childers et al. |
| 5,866,164 A | 2/1999 | Kuczynski et al. |
| 5,906,832 A | 5/1999 | Jao et al. |
| 5,912,268 A | 6/1999 | Guittard et al. |
| 5,914,131 A | 6/1999 | Merrill et al. |
| 5,948,747 A | 9/1999 | Schambil et al. |
| 5,948,787 A | 9/1999 | Merrill et al. |
| 5,993,858 A | 11/1999 | Crison et al. |
| 5,998,478 A | 12/1999 | Platt |
| 6,004,582 A | 12/1999 | Faour et al. |
| 6,020,000 A | 2/2000 | Wong et al. |
| 6,132,420 A | 10/2000 | Dionne et al. |
| 6,136,345 A | 10/2000 | Grimmett et al. |
| 6,153,678 A | 11/2000 | Dong et al. |
| 6,174,547 B1 | 1/2001 | Dong et al. |
| 6,183,466 B1 | 2/2001 | Wong et al. |
| 6,228,863 B1 | 5/2001 | Palermo et al. |
| 6,245,357 B1 * | 6/2001 | Edgren et al. .......... 424/473 |
| 6,254,891 B1 | 7/2001 | Anaebonam et al. |
| 6,270,787 B1 | 8/2001 | Ayer |
| 6,283,953 B1 | 9/2001 | Ayer et al. |
| 6,284,274 B1 | 9/2001 | Merrill et al. |
| 6,287,295 B1 | 9/2001 | Chen et al. |
| 6,316,028 B1 | 11/2001 | Wong et al. |
| 6,333,050 B2 | 12/2001 | Wong et al. |
| 6,342,245 B1 | 1/2002 | Baert et al. |
| 6,342,249 B1 | 1/2002 | Wong et al. |
| 6,365,183 B1 | 4/2002 | Edgren et al. |
| 6,368,626 B1 | 4/2002 | Bhatt et al. |
| 6,375,978 B1 | 4/2002 | Kleiner et al. |
| 6,387,404 B2 | 5/2002 | Oshlack et al. |
| 6,485,748 B1 | 11/2002 | Chen et al. |
| 6,491,683 B1 | 12/2002 | Dong et al. |
| 6,491,945 B1 | 12/2002 | Childers et al. |
| 6,491,949 B2 | 12/2002 | Faour et al. |
| 6,495,162 B2 | 12/2002 | Cheng et al. |
| 6,586,458 B1 | 7/2003 | Plachetka |
| 6,592,900 B1 | 7/2003 | Buhler et al. |
| 6,610,323 B1 | 8/2003 | Lundberg et al. |
| 6,669,955 B2 | 12/2003 | Chungi et al. |
| 6,893,660 B2 | 5/2005 | Li et al. |
| 7,195,778 B2 | 3/2007 | Fleshner-Barak et al. |
| 7,457,343 B2 | 11/2008 | Vancoille |
| 2001/0012847 A1 | 8/2001 | Lam et al. |
| 2001/0024658 A1 | 9/2001 | Chen et al. |
| 2001/0026809 A1 | 10/2001 | Oshlack et al. |
| 2001/0031279 A1 | 10/2001 | Cruz et al. |
| 2002/0058050 A1 | 5/2002 | Sackler et al. |
| 2002/0071863 A1 | 6/2002 | Dong et al. |
| 2003/0077320 A1 | 4/2003 | Childers et al. |
| 2003/0092724 A1 * | 5/2003 | Kao et al. .................. 514/282 |
| 2003/0190358 A1 | 10/2003 | Oshlack et al. |
| 2003/0198619 A1 | 10/2003 | Dong et al. |
| 2003/0224051 A1 | 12/2003 | Fink et al. |
| 2003/0232078 A1 | 12/2003 | Dong et al. |
| 2004/0247677 A1 | 12/2004 | Oury et al. |
| 2005/0020613 A1 * | 1/2005 | Boehm et al. .................. 514/282 |
| 2005/0089570 A1 | 4/2005 | Cruz et al. |
| 2005/0112195 A1 | 5/2005 | Cruz et al. |
| 2005/0158382 A1 | 7/2005 | Cruz et al. |
| 2006/0099257 A1 | 5/2006 | Langridge et al. |
| 2006/0251721 A1 | 11/2006 | Cruz et al. |
| 2007/0259033 A1 | 11/2007 | Cruz |
| 2008/0031901 A1 | 2/2008 | Qiu et al. |
| 2010/0221293 A1 | 9/2010 | Cruz et al. |
| 2011/0166171 A1 | 7/2011 | Qiu et al. |

FOREIGN PATENT DOCUMENTS

| | | |
|---|---|---|
| EP | 0293066 A2 | 11/1988 |
| EP | 174726 B1 | 4/1989 |
| EP | 166287 B1 | 8/1989 |
| EP | 220805 B1 | 9/1989 |
| EP | 367746 A2 | 5/1990 |
| EP | 377518 A2 | 7/1990 |
| EP | 475536 A1 | 3/1992 |
| EP | 367746 B1 | 2/1994 |
| EP | 631781 A1 | 1/1995 |
| EP | 377518 B1 | 2/1996 |
| EP | 475536 B1 | 4/1997 |
| EP | 958812 A1 | 11/1999 |
| EP | 1027888 A2 | 8/2000 |
| GB | 2163747 A | 3/1986 |
| WO | WO9004965 A1 | 5/1990 |
| WO | WO9006925 A1 | 6/1990 |
| WO | WO9119711 A1 | 12/1991 |
| WO | WO9119712 A1 | 12/1991 |
| WO | WO9324154 A1 | 12/1993 |
| WO | WO9427988 A1 | 12/1994 |
| WO | WO9501977 A1 | 1/1995 |
| WO | WO9514460 A1 | 6/1995 |
| WO | WO9534285 A1 | 12/1995 |
| WO | WO9601629 A1 | 1/1996 |
| WO | WO9610996 A1 | 4/1996 |
| WO | WO9635414 A1 | 11/1996 |
| WO | WO9806380 A2 | 2/1998 |
| WO | WO9814168 A2 | 4/1998 |
| WO | WO9823263 A1 | 6/1998 |
| WO | WO9944591 A1 | 9/1999 |
| WO | WO9955313 A1 | 11/1999 |
| WO | WO9962496 A1 | 12/1999 |
| WO | WO0035426 A2 | 6/2000 |
| WO | WO0132148 A1 | 5/2001 |
| WO | WO0151038 A1 | 7/2001 |
| WO | WO0205647 A1 | 1/2002 |
| WO | WO0234240 A2 | 5/2002 |
| WO | WO02087512 A2 | 11/2002 |
| WO | WO03092648 A1 | 11/2003 |
| WO | WO03101384 A2 | 12/2003 |
| WO | WO2004002448 A1 | 1/2004 |
| WO | WO2004010970 A1 | 2/2004 |
| WO | WO2004056337 A2 | 7/2004 |
| WO | WO2007085024 A2 | 7/2007 |
| WO | WO2008011169 A2 | 1/2008 |

OTHER PUBLICATIONS

Dalton, et al., "Predictive Ability of Level A in Vitro-in Vivo Correlation for RingCap Controlled-Release Acetaminophen Tablets," Pharmaceutical Research, 2001, vol. 18 (12), pp. 1729-1732.

Donrrow, et al., "Enhancement of Permeability of Ethyl Cellulose Films for Drug Penetration," Journal of Pharmacy and Pharmacology, 1975, vol. 27 (9), pp. 633-646.

Donbrow, et al., "Zero Order Drug Delivery from Double-Layered Porous Films: Release Rate Profiles from Ethyl Cellulose, Hydroxypropyl Cellulose and Polyethylene Glycol Mixtures," Journal of Pharmacy and Pharmacology, 1980, vol. 32 (7), pp. 463-470.

Fried, R., "Polymer Science and Technology (Englewood Cliffs. N.J. 07632, Prentice Hall PTR, 1995)," 1995, pp. 16-18.

Gennaro, A., ed., Oral Solid Dosage Forms: Remington's Pharmaceutical Sciences, 18th Edition, Mack Publishing Company, 1990, pp. 1635-1637.
Gimbel, et al., "Efficacy and Tolerability of Celecoxib Versus Hydrocodone/Acetaminophen in the Treatment of Pain After Ambulatory Orthopedic Surgery in Adults," Clinical Therapeutics, 2001, vol. 23 (2), pp. 228-241.
GlaxoSmithKline-Submission to the Medicines Classification Committee for Reclassification of a Medicine, Classification of Paracetamol in modified release tablets containing 665 mg or less, as a Pharmacy only Medicine, pp. 1-21, Jul. 2001.
Heading, et al., "The Dependence of Paracetamol Absorption on the Rate of Gastric Emptying," British Journal of Pharmacology, 1973, vol. 47, pp. 415-421.
Higuchi, et al., "Rate of Release of Medicaments from Ointment Bases Containing Drugs in Suspension," Journal of Pharmaceutical Sciences, 1961, vol. 50, pp. 874-875.
Hixon, et al., "Sizing Materials by Crushing and Grinding," Chemical Engineering, 1990, pp. 91-103.
INTERNATIONAL SEARCH REPORT for Application No. PCT/US2004/031420, mailed on Feb. 15, 2005, 5 pages.
INTERNATIONAL SEARCH REPORT for Application No. PCT/US2004/031475, mailed on Feb. 15, 2005, 6 pages.
INTERNATIONAL SEARCH REPORT for Application No. PCT/US2004/031509, mailed on Feb. 17, 2005, 5 pages.
Jackson, et al., "Drug-Excipient Interactions and their Affect on Absorption," Pharmaceutical Sciences Technology, 2000, vol. 3 (10), pp. 336-345.
Kimura, et al., "Drug Absorption from Large Intestine: Physicochemical Factors Governing Drug Absorption," Biological & Pharmaceutical Bulletin, 1994, vol. 17 (2), pp. 327-333.
Krishnaiah, et al., "A Three-Layer Guar Gum Matrix Tablet for Oral Controlled Delivery of Highly Soluble Metoprolol Tartrate," International Journal of Pharmaceutics, 2002, vol. 241 (2), pp. 353-366.
Kwakye, et al., "Gamma Scintigraphic Evaluation of Film-Coated Tablets Intended for Colonic or Biphasic Release," International Journal of Pharmaceutics, 2004, vol. 270, pp. 307-313.
Mandelkern, L., "Structural Features and Preparation" in: An Introduction to Macromolecules, 2nd edition, Springer-Verlag, 1983, pp. 19-27.
McCutcheon, Detergents and Emulsifiers, MC Publishing Co., 1979, Table of Contents.
McNeil's background package on acetaminophen for the Sep. 19, 2002 Nonprescription Drugs Advisory Committee Meeting that was announced in the Federal Register of Aug. 20, 2002. Available at < http://www.fda.gov/ohrms/docket/ac/02/briefing/3882B1_13_McNeil_Acetaminophen.pdf >. Accessed Mar. 14, 2006.
Nandi, et al., "Synergistic Effect of PEG-400 and Cyclodextrin to Enhance Solubility of Progesterone," AAPS PharmSciTech, 2003, vol. 4 (1), pp. 1-5.
Parrott, E., "Milling of Pharmaceutical Solids," Journal of Pharmaceutical Sciences, 1974, vol. 63 (6), pp. 813-829.
Perry, et al., "Introduction to Screening and Wet Classification" in: Perry's Chemical Engineers' Handbook, 6th Edition, McGraw-Hill Book Company, 1984, pp. 21.13-21.19.
Qiu, et al., "Design and Evaluation of Layered Diffusional Matrices for Zero-Order Sustainedrelease," Journal of Controlled Release, 1998, vol. 51, pp. 123-130.
Ripple, E., "Powders" in: Remington's Pharmaceutical Sciences, 17th edition, Gennaro A.R., ed., Mack Publishing Company, 1985, pp. 1585-1602.
Rouse, B., "Cellulose Esters, Organic" in: Encyclopedia of Polymer Science and Technology, Tennessee Eastman Company, 1964, vol. 3, pp. 325-354.
Rowe, R., "The Effect of the Molecular Weight of Ethyl Cellulose on the Drug Release Properties of Mixed Films of Ethyl Cellulose and Hydroxypropyl Methylcellulose," International Journal of Pharmaceutics, 1986, vol. 29, pp. 37-41.
Sako, et al., "Influence of Water Soluble Fillers in Hydroxypropylmethylcellulose Matrices on in Vitro and in Vivo Drug Release," Journal of Controlled Release, 2002, vol. 81, pp. 165-172.
Santus, et al., "Osmotic Drug Delivery: A Review of the Patent Literature," Journal of Controlled Release, 1995, vol. 35, pp. 1-21.
Sawada, et al., "A New Index, the Core Erosion Ratio, of Compression-Coated Timed-Release Tablets Predicts the Bioavailability of Acetaminophen," International Journal of Pharmaceutics, 2003, vol. 265, pp. 55-63.
Shimono, et al., "Chitosan Dispersed System for Colon-Specific Drug Delivery," International Journal of Pharmaceutics, 2002, vol. 245, pp. 45-54.
Torrado, et al., "Correlation of in Vitro and in Vivo Acetaminophen Availability from Albumin Microaggregates Oral Modified Release Formulations," International Journal of Pharmaceutics, 2001, vol. 217, pp. 193-199.
U.S. Appl. No. 13/652,149, filed Oct. 15, 2012.
Wurster, D., "Air-Suspension Technique of Coating Drug Particles," Journal of American Pharmaceutical Association, 1959, vol. 48 (8), pp. 451-459.
Wurster, D., "Preparation of Compressed Tablet Granulations by the Air-Suspension Technique II," Journal of the American Pharmaceutical Association, 1960, vol. 49 (2), pp. 82-84.
Yamada, et al., "Evaluation of Gastrointestinal Transit Controlled-Beagle Dog as a Suitable Animal Model for Bioavailability Testing of Sustained-Release Acetaminophen Dosage Form," International Journal of Pharmaceutics, 1995, vol. 119, pp. 1-10.
Boylan J.C., et al., "Hydroxypropyl Methylcellulose" in: Handbook of Pharmaceutical Excipients, 1st Edition, American Pharmaceutical Association, 1986, pp. 138-140.
Boylan J.C., et al., "Microcrystalline Cellulose" in: Handbook of Pharmaceutical Excipients, 1st Edition, American Pharmaceutical Association, 1986, pp. 53-55.
Co-pending U.S. Appl. No. 10/979,687, filed Nov. 1, 2004.
Final Office Action mailed Apr. 2, 2008 for U.S. Appl. No. 10/949,141, filed Sep. 24, 2004.
Final Office Action mailed Aug. 14, 2006 for U.S. Appl. No. 10/949,141, filed Sep. 24, 2004.
Final Office Action mailed May 15, 2012 for U.S. Appl. No. 13/050,077, filed Mar. 17, 2011.
Final Office Action mailed Feb. 19, 2009 for U.S. Appl. No. 10/949,141, filed Sep. 24, 2004.
Final Office Action mailed Sep. 21, 2010 for U.S. Appl. No. 11/737,904, filed Apr. 20, 2007.
Final Office Action mailed Mar. 25, 2010 for U.S. Appl. No. 10/949,141, filed Sep. 24, 2004.
Fried, R.F, "Polymer Science and Technology (Englewood Cliffs. N.J. 07632, Prentice Hall PTR, 1995)," 1995, pp. 16-18.
Hiemenz P.C., "The Chains and Averages of Polymers" in: Polymer Chemistry The Basic Concepts, Marcel Dekker Inc., 1984, pp. 34-43.
International Preliminary Report on Patentability and Written Opinion for Application No. PCT/US2004/031420, mailed on Mar. 27, 2006, 9 pages.
International Preliminary Report on Patentability and Written Opinion for Application No. PCT/US2008/060564, mailed on Oct. 20, 2009, 6 pages.
International Preliminary Report on Patentability and Written Opinion for Application No. PCT/US2008/060565, mailed date on Oct. 20, 2009, 6 pages.
International Search Report for Application No. PCT/US2008/060564, mailed on Oct. 16, 2009, 3 pages.
Jackson K., et al., "Drug-Excipient Interactions and their Affect on Absorption," Pharmaceutical Sciences Technology, 2000, vol. 3 (10), pp. 336-345.
Mandelkern L., "Structural Features and Preparation" in: An Introduction to Macromolecules, 2nd edition, Springer-Verlag, 1983, pp. 19-27.
McCutcheon's Detergents and Emulsifiers, International Edition, MC Publishing Co., 1979, Table of Contents.
Nandi I., et al., "Synergistic Effect of Peg-400 and Cyclodextrin to Enhance Solubility of Progesterone," AAPS PharmSciTech, 2003, vol. 4 (1), pp. 1-5.
Nikitin N.I., "A General Survey of Physiochemical Properties of Cellulose" in: The Chemistry of Cellulose and Wood, Israel Program for Scientific Translations, 1966, pp. 62-71.

Non-Final Office Action mailed Sep. 2, 2009 for U.S. Appl. No. 11/480,124, filed Jun. 30, 2006.

Non-Final Office Action mailed Nov. 3, 2005 for U.S. Appl. No. 10/949,141, filed Sep. 24, 2004.

Non-Final Office Action mailed Sep. 3, 2008 for U.S. Appl. No. 10/949,141, filed Sep. 24, 2004.

Non-Final Office Action mailed Jan. 4, 2010 for U.S. Appl. No. 11/737,904, filed Apr. 20, 2007.

Non-Final Office Action mailed Aug. 18, 2011 for U.S. Appl. No. 12/716,086, filed Mar. 3, 2010.

Non-Final Office Action mailed Jun. 20, 2007 for U.S. Appl. No. 10/949,141, filed Sep. 24, 2004.

Non-Final Office Action mailed Jun. 25, 2009 for U.S. Appl. No. 10/949,141, filed Sep. 24, 2004.

Non-Final Office Action mailed Nov. 25, 2011 for U.S. Appl. No. 13/050,077, filed Mar. 17, 2011.

Non-Final Office Action mailed Sep. 30, 2011 for U.S. Appl. No. 10/949,141, filed Sep. 24, 2004.

O'Connor R.E., et al., "Powders" in: Remington's Pharmaceutical Sciences, 18th edition, Gennaro A.R., ed., Mack Publishing Company, 1990, pp. 1615-1632.

Rowe R.C., et al., "Copovidone" in: Handbook of Pharmaceutical Excipients, 5th Edition, Pharmaceutical Press, 2006, pp. 201-203.

* cited by examiner

SUSTAINED RELEASE FORMULATIONS OF OPIOID AND NONOPIOID ANALGESICS

This application is a continuation-in-part of U.S. patent application Ser. No. 10/949,141, which is incorporated by reference in this application in its entirety. In addition, all patents, patent applications and literature references cited in the specification are also incorporated by reference in their entirety. In the case of any inconsistency, the present disclosure, including definitions, will prevail.

FIELD OF THE INVENTION

The present invention provides monoeximic solid dosage forms for administering pharmaceutical agents, methods for preparing said dosage forms and methods for providing therapeutic agents to patients in need of treatment thereof.

BACKGROUND OF THE INVENTION

Extended release of acetaminophen ("APAP", paracetamol) and hydrocodone ("HC") that can be administered twice a day (BID dosing) has previously been achieved using osmotic systems, two release-component matrix systems and two release-component coated reservoir systems as disclosed in U.S. Patent Application Publication No. 2005/0158382 A1 to Cruz et al. These systems generally require complicated manufacturing processes that can be inefficient, expensive or both. Therefore, it would be advantageous to reduce the complexity of these prior dosage forms, reduce the number of excipients used in these formulations and/or reduce the processing steps used to manufacture these formulations while achieving the performance (including the safety and efficacy) of the controlled release dosage forms disclosed in Cruz et al.

SUMMARY OF THE INVENTION

In one aspect, the present invention provides a sustained release monoeximic dosage form that includes a single rate controlling mechanism. The single rate controlling mechanism included in said dosage form comprises at least one pharmaceutically acceptable hydrophobic rate controlling material, a pharmaceutically acceptable hydrophilic rate controlling material, a polymeric rate controlling material, a non-polymer rate controlling material, or any combinations thereof.

The dosage form of the present invention is suitable for twice daily oral dosing to a human and comprises a therapeutically effective amount of Hydrocodone (defined hereinafter) and a therapeutically effective amount of acetaminophen. The amount of acetaminophen in said dosage form is preferably between about 20 and about 40 times by weight of Hydrocodone. Moreover, when the dosage form is administered to a population of healthy human volunteers, who are residents of North America, the dosage form is capable of providing analgesia for at least about 12 hours and produces a plasma profile after a single dose of the dosage form characterized by:

a mean AUC for Hydrocodone from about 11.3 to about 18.7 ng*hr/mL per mg of Hydrocodone and a mean AUC for acetaminophen from about 28.7 to about 53.5 ng*hr/mL per mg of acetaminophen, and a Cmax for Hydrocodone of between about 0.6 ng/mL per mg of Hydrocodone to about 1.4 ng/mL per mg of Hydrocodone, and a Cmax for acetaminophen of between about 2.8 ng/mL per mg of acetaminophen and 7.9 ng/mL/mg of acetaminophen.

Additionally, the dosage form of the present invention, after administration thereof to a population of healthy human volunteers, is preferably capable of reducing pain intensity in a patient within about 1 hour. Similarly, the dosage form of the present invention is preferably capable of producing a statistically significant reduction in the pain intensity of a population of North American residents in moderate to severe pain within about 1 hour after administration of the dosage form to each individual in the population.

The dosage form of the present invention is preferably adapted to release about 19% to about 49% of the Hydrocodone and acetaminophen in vitro within 0.75 hours. Moreover, the dosage form preferably releases at least 90% of the Hydrocodone and acetaminophen in vitro within 12 hours, and more preferably releases at least 90% of the Hydrocodone and acetaminiophen in vitro within 9 hours, and most preferably releases at least 90% of the Hydrocodone within about 8 hours.

The dosage form of the present invention optionally comprises about 500 mg of acetaminophen and about 15 mg of hydrocodone bitartrate.

Additionally, the dosage form can be administered to a human patient or to a volunteer who is a poor CYP2D6 metabolizer or a non-poor CYP2D6 metabolizer. In a non-poor CYP2D6 metabolizer, the dosage form produces a Cmax for hydromorphone (a metabolite of Hydrocodone) in the human of between about 0.12 ng/ml and about 0.35 ng/ml after a single dose of 30 mg of Hydrocodone.

Additionally, the dosage form of the present invention is preferably capable of producing the following mean blood plasma profiles in a population of at least 10 human volunteers: (a) a plasma concentration for Hydrocodone that is between about 11.0 ng/ml and about 27.4 ng/ml 12 hours after administration of a single 30 mg dose of Hydrocodone; (b) a plasma concentration for acetaminophen that is between about 0.7 µg/ml and about 2.5 µg/ml 12 hours after administration of a single 1000 mg dose of acetaminophen; (c) a plasma concentration profile that exhibits a width at half height for Hydrocodone of between about 6.4 hours and about 19.6 hours after administration of a single dose of 30 mg of Hydrocodone; (d) a plasma concentration profile that exhibits a width at half height for Hydrocodone of between about 8.4 hours and about 19.6 hours after administration of a single dose of 30 mg of Hydrocodone; and (e) a plasma concentration profile that exhibits a width at half height for acetaminophen of between about 0.8 hours and about 12.3 hours after administration of a single dose of 1000 mg of acetaminophen.

Another aspect of the invention disclosed herein provides a pharmaceutical composition comprising at least two sustained release subunits (hereinafter an "SRSR pharmaceutical composition"). Specifically, the SRSR pharmaceutical composition comprises a first sustained release subunit that comprises acetaminophen, Hydrocodone or both acetaminophen and Hydrocodone and a second sustained release subunit that comprises acetaminophen, Hydrocodone or both acetaminophen and Hydrocodone. Preferably, either the first subunit or the second subunit comprises acetaminophen and Hydrocodone. More preferably, both the first subunit and the second subunit each comprise acetaminophen and Hydrocodone. Each of the first and second subunits can contain a single rate controlling mechanism. The single rate controlling mechanism that can be included in each of the subunits comprises at least one pharmaceutically acceptable hydrophobic rate controlling material, a pharmaceutically acceptable hydrophilic rate controlling material, a polymeric rate controlling material, a non-polymer rate controlling material, or any combinations thereof.

Each of the first and second subunits of the SRSR pharmaceutical composition are preferably monoeximic subunits. The monoeximic subunits can be the same or different. Each of the monoeximic subunits can be of any suitable form, and are preferably selected from a matrix system, an osmotic system, a reservoir system, and can optionally be selected so as to form a combination of at least one matrix system, an osmotic system or a reservoir system, and another subunit independently selected from the same list. For example, one of the monoeximic subunits can comprise a matrix system and the other monoeximic subunit can comprise an osmotic system. Alternatively, one of the monoeximic subunit can comprise a matrix system and the other monoeximic subunit can comprise a reservoir system. By way of yet another alternative, one of the monoeximic subunit can comprise a reservoir system and the other monoeximic subunit can comprise an osmotic system.

The pharmaceutical composition of the present invention is suitable for twice daily oral dosing to a human and comprises a therapeutically effective amount of Hydrocodone and a therapeutically effective amount of acetaminophen. The amount of acetaminophen in said pharmaceutical composition is between about 20 and about 40 times by weight of Hydrocodone. Moreover, when said pharmaceutical composition is administered to a population of healthy human volunteers (who are residents of North America), the pharmaceutical composition is capable of providing analgesia for at least about 12 hours and produces a plasma profile characterized by:

a mean AUC for Hydrocodone from about 11.3 to about 18.7 ng*hr/mL per mg of Hydrocodone and a mean AUC for acetaminophen from about 28.7 to about 53.5 ng*hr/mL per mg of acetaminophen after a single dose, and a Cmax for Hydrocodone of between about 0.6 ng/mL per mg of Hydrocodone to about 1.4 ng/mL per mg of Hydrocodone, and a Cmax for acetaminophen of between about 2.8 ng/mL per mg of acetaminophen and 7.9 ng/mL/mg of acetaminophen after a single dose.

Additionally, the pharmaceutical composition of the present invention, after administration thereof to a population of healthy human volunteers, is capable of reducing pain intensity in a patient within about 1 hour.

The pharmaceutical composition of the present invention is adapted to release about 19% to about 49% of the Hydrocodone and acetaminophen in vitro within 0.75 hours. Moreover, said pharmaceutical composition releases at least 90% of the Hydrocodone and acetaminophen in vitro within 8 hours or alternatively, releases at least 90% of the Hydrocodone and acetaminophen in vitro within 12 hours.

The pharmaceutical composition of the present invention can comprises about 500 mg of acetaminophen and about 15 mg of hydrocodone bitartrate.

Additionally, the dosage form can be administered to a human patient or to a volunteer who is a poor CYP2D6 metabolizer or a non-poor CYP2D6 metabolizer. In a non-poor CYP2D6 metabolizer, the pharmaceutical composition produces a Cmax for hydromorphone (which is a metabolite of Hydrocodone) in the human of between about 0.12 ng/ml and about 0.35 ng/ml after a single dose of 30 mg of Hydrocodone.

Additionally, the SRSR pharmaceutical composition of the present invention is preferably capable of producing the following mean blood plasma profiles in a population of at least 10 human volunteers: (a) a plasma concentration for Hydrocodone that is between about 11.0 ng/ml and about 27.4 ng/ml 12 hours after administration of a single 30 mg dose of Hydrocodone; (b) a plasma concentration for acetaminophen that is between about 0.7 μg/ml and about 2.5 μg/ml 12 hours after administration of a single 1000 mg dose of acetaminophen; (c) a plasma concentration profile that exhibits a width at half height for Hydrocodone of between about 6.4 hours and about 19.6 hours after administration of a single dose of 30 mg of Hydrocodone; (d) a plasma concentration profile that exhibits a width at half height for Hydrocodone of between about 8.4 hours and about 19.6 hours after administration of a single dose of 30 mg of Hydrocodone; and (e) a plasma concentration profile that exhibits a width at half height for acetaminophen of between about 0.8 hours and about 12.3 hours after administration of a single dose of 1000 mg of acetaminophen.

DETAILED DESCRIPTION OF THE PRESENT INVENTION

Definitions

Figure 1:
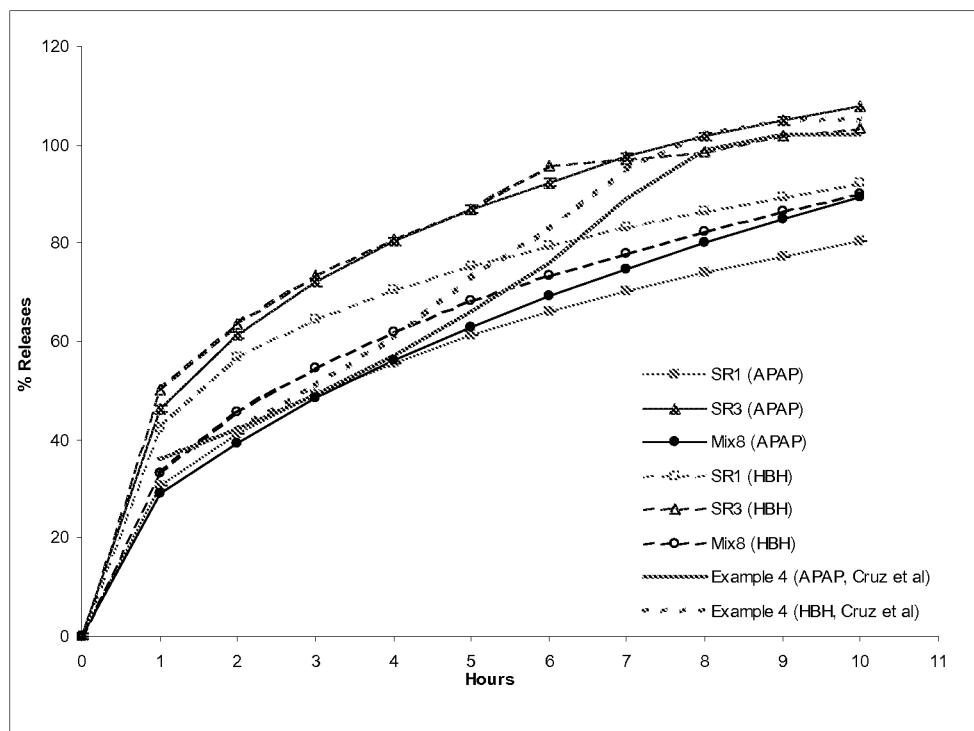
FIG. 1 shows the in vitro drug release of a multi-unit monoeximic extended release tablets containing APAP and hydrocodone bitartrate hemipentahydrate ("HBH").

As used herein and in the claims, the singular forms "a", "and" and "the" include plural referents unless the context dictates otherwise such as with respect to the number of drug release components employed by a dosage form. For example, reference to "a carrier" includes two or more carriers; reference to "a pharmaceutical agent" includes two or more pharmaceutical agents and so forth.

As used herein, the term "AUC" refers to the mean area under the concentration time curve from time zero to infinity following a single dose, calculated using the trapezoidal rule, wherein at least 10 health, North American volunteers are tested. $AUC = AUCt + C_{last}/k$, where $C_{last}$ is the last observed concentration and k is the calculated elimination rate constant.

As used herein, the term "AUCt" refers to the area under the concentration time curve from the time of administration of the dosage form to the time of the last observed concentration calculated using the trapezoidal rule.

As used herein, the phrase "breakthrough pain" refers to pain which a patient experiences despite the fact that the patient is being administered generally effective amounts of an analgesic.

As used herein, the term "C12" is the plasma concentration of the referent drug observed 12 hours after administration of a single dose, or the indicated number of doses, of a drug dosage form or pharmaceutical composition.

As used herein, the term "Cmax" refers to the plasma concentration of the referent drug at Tmax expressed herein as ng/mL and μg/mL, respectively, produced by the oral ingestion of a single dose, or indicated number of doses, of the dosage form or pharmaceutical composition, such as the dosage forms and compositions of the present invention or the every four-hour comparator (NORCO® 10 mg hydrocodone/325 mg acetaminophen). Unless specifically indicated, Cmax refers to the overall maximum observed concentration.

As used herein the terms "deliver" and "delivery" refer to separation of the pharmaceutical agent from the dosage form or composition, wherein the pharmaceutical agent is able to dissolve in the fluid of the environment of use.

As used herein, the phrase "dosage form" refers to a pharmaceutical composition, formulation, or device comprising one or more pharmaceutical agents or one or more pharmaceutically acceptable acid addition salts thereof, the composition, formulation, or device optionally containing one or more pharmacologically inactive ingredients, such as, but not limited to, pharmaceutically acceptable excipients such as polymers, suspending agents, surfactants, disintegrants, dissolution modulation components, binders, diluents, lubricants, stabilizers, antioxidants, osmotic agents, colorants, plasticizers, coatings and the like, that are used to manufacture and deliver active pharmaceutical agents.

As used herein, the phrase "effective pain management" refers to an objective evaluation of a human patient's response (namely, pain experienced versus side effects) to analgesic treatment by a physician as well as subjective evaluation of therapeutic treatment by the patient undergoing such treatment.

As used herein, the capitalized term "Hydrocodone" generally refers to any pharmaceutically acceptable hydrocodone moiety, including, without limitation, hydrocodone free base, a pharmaceutically acceptable addition salt of hydrocodone, or a pharmaceutically acceptable ester of hydrocodone, and is preferably hydrocodone bitartrate or hydrocodone bitartrate hemipentahydrate. However, specific references to the weight of Hydrocodone refer to the weight of hydrocodone bitartrate hemipentahydrate, which can be substituted by a molar equivalent of another suitable form of hydrocodone. Additionally, when referring to hydrocodone concentrations found in the blood of a volunteer, patient, or population, the term hydrocodone is used herein because it is generally not plausible to determine the nature and quantity of counter ions and esters associated with the hydrocodone found in the blood at the moment of assay. Similarly, references to hydrocodone bitartrate refer to any suitable hydrate of this moiety, except when referring to the weight of this moiety which always refers to the hemipentahydrate herein.

As used herein, the phrase "minimum effective analgesic concentration" refers to the minimum effective therapeutic plasma level of the drug at which at least some pain relief is achieved in a given patient. It is well understood by those skilled in the medical arts that pain measurement is highly subjective and that great individual variations may occur among patients.

As used herein, unless further specified, the term "a patient" refers to an individual patient or a population of patients in need of treatment for a disease or disorder. However, for determining whether a dosage form or formulation is adapted to deliver a pharmacokinetic property, the standard test conditions to be employed require that the average values (e.g., mean) be obtained when the drug formulation is administered to at least 10 healthy human volunteers that are residents of the United States, Canada, or western Europe, wherein said volunteers are not vegetarians, on a diet substantially deprived of a macronutrient, or taking any other drugs or substances that are known to affect the absorption, distribution, metabolism or excretion of an opioid analgesic or acetaminophen.

As used herein the phrase "pharmaceutically acceptable acid addition salt" or "pharmaceutically acceptable salt", which are used interchangeably herein refers to those salts in which the anion does not contribute significantly to the toxicity or pharmacological activity of the salt, and, as such, they are the pharmacological equivalent of the base form of the active agent. Examples of pharmaceutically acceptable acids that are useful for the purposes of salt formation include, but are not limited to, hydrochloric, hydrobromic, hydroiodic, sulfuric, citric, tartaric, methanesulfonic, fumaric, malic, maleic and mandelic acids. Pharmaceutically acceptable salts further include mucate, N-oxide, sulfate, acetate, phosphate dibasic, phosphate monobasic, acetate trihydrate, bi(heptafluorobutyrate), bi(methylcarbamate), bi(pentafluoropropionate), bi(pyridine-3-carboxylate), bi(trifluoroacetate), bitartrate, chlorhydrate, and sulfate pentahydrate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, and procaine, aluminum, calcium, lithium, magnesium, potassium, sodium propionate, zinc and the like.

A drug "release rate" as used herein refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions in a USP Type II apparatus and immersed in 900 ml of simulated intestinal fluid (SIF) at pH 6.8 and equilibrated in a constant temperature water bath at 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

Unless otherwise specified, a drug release rate obtained at a specified time refers to the in vitro drug release rate obtained at the specified time following implementation of an appropriate dissolution test. The time at which a specified percentage of the drug within a dosage form has been released may be referenced as the "$T_x$" value, where "x" is the percent of drug that has been released. For example, a commonly used reference measurement for evaluating drug release from dosage forms or pharmaceutical compositions is the time at which 90% of drug within the dosage form or pharmaceutical composition has been released. This measurement is referred to as the "$T_{90}$" for the dosage form.

Unless specifically designated as a "single dose" or at "steady-state", the pharmacokinetic parameters disclosed and claimed herein encompass both single dose and steady state conditions.

As used herein, the phrase "a single rate controlling mechanism" refers to one or more pharmaceutically acceptable rate controlling materials, such as, but not limited to, one or more polymers, one or more excipients or other materials, that are incorporated in a composition (such as, but not limited to, a dosage form) to modify the rate of release of an opioid analgesic, a nonopioid analgesic or both an opioid analgesic and a nonopioid analgesic from said composition. For example, the one or more pharmaceutically acceptable rate controlling materials can be a hydrophobic rate controlling material, a hydrophilic rate controlling material, a polymeric rate controlling material, a pharmaceutically acceptable non-polymer rate controlling material or any combinations thereof. Sustained release pharmaceutical compositions are sometimes classified as "matrix", "reservoir", or "osmotic" mechanisms (or systems), depending on the type or principle type of rate controlling mechanism employed by the formulation.

As used herein, the phrase "sustained release" refers to the release of the drug from the dosage form subunit, a dosage form, or pharmaceutical composition over a period substantially longer than one hour, such as about two hours or longer. Generally, the sustained release of drug from the inventive compositions occurs at such a rate that blood (for example, plasma) concentrations in a patient administered the dosage form or pharmaceutical composition are sufficient to mitigate painover a period of time of at least about 12 hours.

As used herein, the phrase "Tmax" refers to the time which elapses after administration of the dosage form or pharmaceutical composition at which the plasma concentration of an opioid analgesic (such as hydrocodone), a nonopioid analgesic (such as acetaminophen), or an opioid analgesic and a nonopioid analgesic attain the maximum plasma concentrations.

As used herein, the phrase "zero order plasma profile" refers to a substantially flat or unchanging amount of a particular drug in the plasma of a patient over a particular time interval. Generally, a zero order plasma profile will vary by no more than about 30%, preferably, by no more than about 10%, from one time interval to the subsequent time interval.

Unless otherwise indicated, the present invention is not limited to specific excipients, polymers, salts or the like and as such can vary. Moreover, the terminology used herein is for the purpose of describing particular embodiments only and is not intended to limit the scope of the invention.

When a range of values is provided, it is understood that each intervening value, to the tenth of the unit of the lower limit unless the context dictates otherwise, between the upper and lower limit of that range and any other stated or intervening value in that stated range, is encompassed by within the present invention. The upper and lower limits of these smaller ranges may independently be included in the small ranges and are also encompassed within the invention, subject to any specifically excluded limit in the stated range. Where the stated range includes one or both of the limits, ranges excluding either or both of those included limits are also included in the present invention.

For clarity and convenience purposes only, the convention is utilized of designating the time of drug administration or initiation of dissolution testing as zero (0) hours (t=0 hours) and times following administration in appropriate time units, for example, t=30 minutes or t=2 hours, etc.

One skilled in the art will understand that effective analgesia will vary according to many factors, including individual patient variability, health status, such as renal and hepatic sufficiency, physical activity, and the nature and relative intensity of pain.

The Present Invention

In one aspect, the present invention pertains to a monoeximic drug delivery composition, which is used herein interchangeably with the term monoeximic drug delivery system. The term "monoeximic" is comprised of the root words "mono" and "eximic", both of which are from the Greek. "Mono" means one or single. "Eximic" means release. Therefore, as used herein, the term "monoeximic" refers a composition that contains a single (i.e., one) mechanism that controls or modulates the release of something (such as one or more drugs) from said composition.

Specifically, a monoeximic composition is a pharmaceutical composition that comprises a single (namely, one) rate controlling mechanism that controls or modulates the rate of one or more drugs that are released from the dosage form.

The following are considered to be examples of monoeximic drug delivery formulations: (1) a single rate controlling mechanism mixed with a drug and compressed such that the drug is slowly released upon exposure to one or more aqueous solutions (a "monoeximic matrix system"); and (2) (a) a core comprising (i) a drug mixture, the drug mixture comprising an excipient such that the mixture rapidly releases drug upon exposure to one or more aqueous solutions (such as in an aqueous environment), and (ii) an osmotically active mixture that swells in response to absorption of aqueous solutions, and (b) a single rate controlling mechanism surrounding the core with an orifice formed therein, wherein the membrane permits water or liquids to slowly flow into the core, which thereby causes the osmotically active mixture to swell, and which swelling causes the core to be exuded through the orifice into the fluids of the gastrointestinal tract of a human if the human swallows the monoeximic drug delivery composition (a "monoeximic osmotic system").

In contrast, a non-monoeximic dosage form comprises zero or two or more rate controlling mechanisms that modify or control the rate of drug released after administration (such as by swallowing) to a human patient. For example, two monoeximic matrix formulations can be pressed together to form a non-monoeximic drug delivery formulation. In another example, a composition that immediately releases drug upon exposure to one or more aqueous solutions (such as an aqueous environment) could be coated onto a monoeximic osmotic delivery system to form a non-monoeximic drug delivery formulation; an example of such a non-monoeximic drug delivery formulation is described in Example 4 of Cruz et al. Additionally, a dosage form that immediately releases substantially all of one or more active agents in less than about an hour is not a monoexemic composition, but rather is an "immediate release" dosage form.

Both monoeximic and non-monoeximic drug delivery formulations can optionally comprise additional elements or compositions that are not involved in modifying or controlling the rate of drug that is released from the formulation. For example, both monoeximic and non-monoeximic drug delivery formulations can be overcoated with a "color coat" to give a uniform or attractive appearance formulation, be it a tablet, capsule, sachet, or pill. Similarly, both monoeximic and non-monoeximic drug delivery formulations can optionally be formed over an inert tablet core. Such an inert tablet core can preferably be made of a pharmaceutically acceptable material.

The monoeximic drug delivery formulations of the present invention provide a number of benefits that can make them preferable to non-monoeximic drug delivery formulations. Specifically, in monoeximic drug delivery formulations it can be easier to detect manufacturing variances that can lead to variable rates of drug release in one or more aqueous systems. Moreover, quality assurance testing can more easily be performed with monoeximic drug delivery formulations compared to non-monoeximic drug delivery formulations. Additionally, the time and costs associated with making monoeximic drug delivery formulations can be lower because monoeximic drug delivery formulations contain only a single rate controlling mechanism. In contrast, non-monoeximic drug delivery formulations contain two or more rate controlling mechanisms thus increasing the time and cost of manufacturing associated with such formulations. Furthermore, in monoeximic drug delivery formulations there is no need to physically adhere or attach one component of the formulation to another as there is in non-monoeximic drug delivery formulations.

In certain embodiments, the present invention provides a monoeximic oral dosage form for drug delivery that includes a single rate controlling mechanism for administering one or more opioid analgesics and one or more nonopioid analgesics over a sustained period of time with a pharmacokinetic profile that provides analgesia (namely, reduces pain intensity) within about 1 hour after administration of said dosage form to a patient. In addition, the oral dosage form of the present invention provides analgesia for a period of time of at least about 12 hours after administration thereof to a human patient. In view thereof, the dosage form is suitable for twice daily oral dosing. Moreover, the present invention provides a bioavailable monoeximic oral dosage form containing one or more opioid analgesics and one or more nonopioid analgesics, preferably Hydrocodone and acetaminophen, that provides analgesia using a less frequent dosing than the currently available immediate release formulations and more preferably achieves the same dosing frequency and is bioequivalent to the non-monoeximic oral dosage forms described by Cruz et al.

The monoeximic dosage forms of present invention further control moderate to severe pain in human patients that require continuous opioid medications for more than a few days by administering a formulation of Hydrocodone and acetaminophen that provides pharmacokinetic parameters that are consistent with twice daily dosing.

The present invention also provides human patients with a treatment for their pain which provides sufficient plasma levels of one or more opioid analgesics and one or more nonopioid analgesics to provide a reduction in pain intensity within about 1 hour after administration and which treatment further provides sufficient plasma levels of one or more opioid analgesics and one or more nonopioid analgesics to provide pain relief at a later time in the dosage interval when it may be expected that patients may experience breakthrough pain.

The present invention also provides twice-a-day monoeximic dosage forms that provide a plasma concentration profile that exhibits in vitro drug release, in vivo drug absorption or both an in vitro drug release and in vivo drug absorption that is substantially the same as the non-monoeximic dosage forms described in Cruz et al. More specifically, the non-monoeximic dosage forms described in Cruz et al., after administration thereof to a patient, are characterized by a relatively rapid, initial rise in plasma levels of one or more opioid analgesics and one or more nonopioid analgesics, preferably, Hydrocodone and acetaminophen. Moreover, the non-monoeximic dosage forms have demonstrated a reduction in pain within about 1 hour after administration followed by a prolonged delivery period that provides therapeutically effective levels of one or more opioid analgesics and one or more nonopioid analgesics in plasma, thereby providing pain relief both early and during the 12 hour dosing period.

The invention also provides a monoeximic dosage form of Hydrocodone and acetaminophen that includes a single rate controlling mechanism, which when this dosage form is administered to a patient produces a pharmacokinetic profile that is similar to the pharmacokinetic profile of the non-monoeximic dosage forms described by Cruz et al.

As mentioned previously herein, the dosage forms of the present invention are suitable for twice daily oral dosing to a human patient for providing relief from pain. Specifically, the dosage forms comprise an amount of one or more opioid analgesics and an amount of one or more nonopioid analgesics that provides relief from pain for at least about 12 hours. The amount of the one or more nonopioid analgesics in the dosage forms can be between about 20 and about 100 times the amount of one or more opioid analgesics by weight. In certain embodiments, the amount of one or more nonopioid analgesics, which is preferably acetaminophen, is between about 20 and about 40 times the amount of one or more opioid analgesics, which is preferably Hydrocodone, by weight. In particular embodiments, the amount of one or more nonopioid analgesic, which is preferably acetaminophen, is between about 27 and about 34 times the amount of one or more opioid analgesics, which is preferably Hydrocodone, by weight. In a preferred embodiment, the nonopioid analgesic is acetaminophen and the opioid analgesic is Hydrocodone, and more preferably hydrocodone bitartrate. For example, the dosage form can contain about 500 mg of acetaminophen and about 15 mg of hydrocodone bitartrate. Alternatively, by way of another example, the dosage form can contain about 1000 mg of acetaminophen and about 30 mg of hydrocodone bitartrate.

The monoeximic dosage form can release the one or more opioid analgesics and the one or more nonopioid analgesics when the dosage from is exposed to the environment of use as an erodible composition. Alternatively, the monoeximic dosage form can also release the one or more opioid analgesics and one or more non-opioid analgesics via a diffusion chemical-mechanism. In yet another alternative, the dosage form can release the one or more opioid analgesics and one or more non-opioid analgesics with a release mechanism mediated in part by both erosion and diffusion chemical-mechanism.

Any opioid analgesic can be used in the monoeximic dosage forms of the present invention. Particularly preferred opioid analgesics include hydrocodone, hydromorphone, codeine, methadone, oxymorphone, oxycodone, morphine, pharmaceutically acceptable salts thereof, pharmaceutically acceptable esters thereof, and any mixtures thereof. The most preferred opioid analgesics are hydrocodone and salts thereof. Any suitable salt of hydrocodone can be used, however, hydrocodone bitartrate is preferred. In certain embodiments, opioid analgesics other than Hydrocodone can be substituted for Hydrocodone and include without limitation: alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, pharmaceutically acceptable salts thereof, pharmaceutically acceptable esters thereof, and any mixtures thereof.

A wide variety of nonopioid analgesics can be used in combination with the opioid analgesics in the dosage form to provide sustained release of analgesic agents to a patient in need thereof on a twice daily basis. In particular, sparingly soluble nonopioid analgesic agents such as acetaminophen can be employed, particularly at high loading to provide pain relief for an extended period of time. Examples of nonopioid analgesics include pharmaceutically acceptable derivatives of the poorly soluble para-aminophenol derivatives exemplified by acetaminophen, aminobenzoate potassium, aminobenzoate sodium. A preferred nonopioid analgesic agent is acetaminophen. The dose of nonopioid analgesic agents, particularly acetaminophen is typically between about 50 mg and about 1000 mg, and is more typically between about 300 mg and about 500 mg.

As also mentioned previously, the monoeximic dosage forms of the present invention contain a single rate controlling mechanism. The single rate controlling mechanism can comprise one or more rate controlling materials. In particular embodiments, the rate controlling material comprises at least one pharmaceutically acceptable hydrophobic rate controlling material, at least one pharmaceutically acceptable hydrophilic rate controlling material, at least one pharmaceutically acceptable rate controlling polymer such as an pharmaceutically acceptable amphipathic polymer, at least one pharmaceutically acceptable non-polymer rate controlling material, or any combinations thereof. Examples of pharmaceutically acceptable hydrophobic polymers and hydrophilic polymers include, but are not limited to, certain pharmaceutically acceptable resins, pharmaceutically acceptable acrylic polymers, pharmaceutically acceptable cellulose ethers and pharmaceutically acceptable biologically derived materials. Examples of pharmaceutically acceptable non-polymer rate controlling materials include, but are not limited, to certain pharmaceutically acceptable long chain substituted or unsubstituted hydrocarbons. Examples of pharmaceutically acceptable acrylic resins and pharmaceutically acceptable acrylic polymers include, but not limited to, acrylic acid and alkylacrylic acid copolymers (which are also anionic polymers), methyl methacrylate copolymers, ethoxyethyl methacrylates, cyanoethyl methacrylate, poly(acrylic acid), poly(methacrylic acid), methacrylic acid alkylamide copolymer, poly (methyl methacrylate), polymethacrylate, poly(methyl methacrylate) copolymer, polyacrylamide, aminoalkyl methacrylate copolymer, poly(methacrylic acid anhydride), and glycidyl methacrylate co-polymers, methacrylic acid ester copolymers, polyvinyl acetate phthalate (PVAP), polyvinyl acetate and polyvinyl pyrrolidone and polyvinyl alcohol (PVA). Examples of pharmaceutically acceptable cellulose ethers include, but not limited to, hydroxyalkylcelluloses and carboxyalkylcelluloses, such as, hydroxypropylcellulose (HPC), hydroxypropylmethylcellulose (HPMC), hydroxyethylcellulose (HEC), methyl cellulose (MC), ethyl cellulose (EC), cellulose acetate (CA), cellulose acetate butyrate, cellulose acetate propionate, hydroxypropylmethylcellulose phthalate (HPMCP) (which is also an anionic polymer), carboxyl methylcellulose (CMC), cellulose acetate phthalate (CAP) (which is also an anionic polymer). Examples of pharmaceutically acceptable biologically derived materials include, but are not limited to, polysaccharides or their derivatives, such as, but not limited to, gums (such as, xantham gum, locust bean gum), sodium alginate, shellac, zein, and the like. Examples of pharmaceutically acceptable long chain substituted or unsubstituted hydrocarbons include, but not limited to, fatty acid esters, fatty acid glycerides (mono-, di-, and tri-glycerides), stearic acid, glyceryl monostearate, glyceryl behenate, lauryl, myristyl, stearyl, cetyl or cetostearyl alcohol, polyethylene glocol, poly(ethylene oxide) and natural and synthetic waxes (such as, but not limited to, beeswax, glycowax, castor wax and carnauba wax). The rate controlling materials can be any suitable weight percentage of the pharmaceutical composition, and preferably make up between 1% (w/w) to about 70% (w/w) of the pharmaceutical composition.

In certain embodiments, the single rate controlling mechanism exhibits a release rate in vitro of a therapeutically effective amount of an opioid analgesic and a nonopioid analgesic from about 9% to about 55% released after 60 minutes, from about 27% to about 80% released after 240 minutes and from about 45% to about 100% after 480 minutes. In additional embodiments, the single rate controlling mechanism exhibits a release rate in vitro of a therapeutically effective amount of an opioid analgesic and nonopioid analgesic of at least 90% released within about 8 hours. In still other embodiments, the single rate controlling mechanism exhibits a release rate in vitro of a therapeutically effective amount of an opioid analgesic and nonopioid analgesic of at least 90% released within about 12 hours. In other additional embodiments, a tablet containing a single rate controlling mechanism exhibits a release rate of Hydrocodone and acetaminophen from about 25% to about 42% released after 60 minutes, from about 45% to about 82% released after 240 minutes and about 70% to about 100% released after 480 minutes when the dosage form is tested in simulated intestinal fluid (0.05 M phosphate buffer, pH 6.8) using a USP Apparatus II.

Due to the significantly different solubility between Hydrocodone and acetaminophen, the release rate of Hydrocodone and acetaminophen and the mechanism by which each of these drugs is released from a monoeximic dosage form are very different. Specifically, Hydrocodone release is significantly faster than the acetaminophen release and is primarily via a diffusion chemical-mechanism. In particular embodiments, similar release rates of Hydrocodone and acetaminophen can be obtained via incorporation of anionic component in the formulation (such anionic component can be a rate controlling material that comprises the single rate controlling mechanism). Examples of anionic polymers that can be used in the formulation are copolymers of methacrylic acid and methacrylic esters (Eudragit L and S), cellulose acetate phthalate (CAP), hydroxypropyl methylcellulose phthalate (HPMCP), or any combinations thereof. While not desiring to be bound by any particular theory, it is believed that the Hydrocodone ionically interacts with the anionic polymer, which in turn increases the effective size of the Hydrocodone and attenuates release of Hydrocodone mediated by the chemical-mechanism of diffusion.

Unintended, rapid drug release in a short period of time of the entire amount or a significant fraction of the drug contained in a sustained release dosage form is often referred to as "dose dumping". Depending on the therapeutic indication and the therapeutic index of a drug, dose-dumping can pose a significant risk to patients, either due to safety issues or diminished efficacy or both. Generally dose-dumping is observed due to a compromise of the rate controlling mechanism (as opposed to the chemical-diffusion mechanism describing the method by which the single rate controlling mechanism functions).

Some sustained release oral dosage forms exhibit higher in vivo rates of drug delivery when ingested with alcoholic (i.e., ethanolic) beverages (e.g., Palladone). Thus, one might expect a more rapid drug release in the presence of ethanol. However, in particular embodiments, the in vitro dissolution rates of the monoeximic pharmaceutically compositions were found to be slower or remain unchanged in 40% ethanol/60% water buffered at pH 6.8. Thus, the single rate controlling mechanism of the monoeximic dosage forms of the present invention can serve to mitigate the risks of ethanol induced dose dumping of opioid analgesic, such as, Hydrocodone.

The present invention also provides a method for relieving pain in mammal comprising administering to the mammal any embodiment of the monoeximic dosage form disclosed herein.

When administered to a human patient, in certain embodiments, the monoeximic dosage form produces a plasma profile that is not significantly different from the plasma profile of the non-monoeximic dosage forms that are described by Cruz et al. For example, when administered to a human patient, in certain embodiments, the monoeximic dosage form of the present invention is adapted to provide a Cmax for hydrocodone of between about 0.6 ng/mL/mg to about 1.4 ng/mL/mg and a Cmax for acetaminophen of between about 2.8 ng/mL/mg and 7.9 ng/mL/mg after a single dose. In certain other embodiments, the monoeximic dosage form produces a minimum Cmax for hydrocodone of about 0.4 ng/mL/mg to a maximum Cmax for hydrocodone of about 1.9 ng/mL/mg and a minimum Cmax for acetaminophen of about 2.0 ng/mL/mg and maximum Cmax for acetaminophen of about 10.4 ng/mL/mg after a single dose. In additional embodiments, the monoeximic dosage form produces a Cmax for hydrocodone of about 0.6 ng/mL/mg to about 1.0 ng/mL/mg and a Cmax for acetaminophen of about 3.0 ng/mL/mg to about 5.2 ng/mL/mg after a single dose.

When administered to the human patient, in certain embodiments, the monoeximic dosage form is adapted to provide a Tmax for hydrocodone of about 1.9 to about 6.7 hours after a single dose. In certain embodiments, the dosage form produces a Tmax for acetaminophen of about 0.5 hours to 6 hours after a single dose, and in other embodiments, the dosage form produces a Tmax for acetaminophen of about 0.9 to about 2.8 hours after a single dose.

In particular embodiments, when administered to the human patient, the monoeximic dosage form produces an AUC for hydrocodone of between about 9.1 ng*hr/mL/mg to about 19.9 ng*hr/mL/mg and an AUC for acetaminophen of between about 28.6 ng*hr/mL/mg and about 59.1 ng*hr/mL/mg after a single dose. In additional embodiments, the monoeximic dosage form produces a minimum AUC for hydrocodone of about 7.0 ng*hr/mL/mg to a maximum AUC for hydrocodone of about 26.2 ng*hr/mL/mg and a minimum AUC for acetaminophen of about 18.4 ng*hr/mL/mg and maximum AUC for acetaminophen of 79.9 ng*hr/mL/mg after a single dose. In yet other embodiments, the dosage form produces a mean AUC for hydrocodone of about 11.3 ng*hr/mL/mg to about 18.7 ng*hr/mL/mg of hydrocodone bitartrate and a mean AUC for acetaminophen of 28.7 ng*hr/mL/mg to about 53.5 ng*hr/mL/mg after a single dose.

In certain embodiments, the monoeximic dosage form produces a Cmax for hydrocodone of between about 0.6 ng/mL/mg to about 1.4 ng/mL/mg and a Cmax for acetaminophen of between about 2.8 ng/mL/mg and 7.9 ng/mL/mg, and a mean AUC for hydrocodone of between about 11.3 ng*hr/mL/mg to about 18.7 ng*hr/mL/mg and a mean AUC for acetaminophen of between about 28.7 ng*hr/mL/mg and about 53.5 ng*hr/mL/mg after a single dose.

In yet other embodiments, the monoeximic dosage form of the present invention produces a Cmax for hydrocodone of between about 19.6 and 42.8 ng/ml after a single dose of 30 mg hydrocodone, while in other embodiments, the dosage form produces a minimum Cmax for hydrocodone of about 12.7 ng/ml and the maximum Cmax for hydrocodone of about 56.9 ng/mL after a single dose of 30 mg Hydrocodone. In a preferred embodiment, the dosage form produces a Cmax for hydrocodone of between about 19.6 and 31 ng/ml after a single dose of 30 mg Hydrocodone.

In other embodiments, the monoeximic dosage form produces a Cmax for acetaminophen of between about 3.0 and about 7.9 µg/ml after a single dose of 1000 mg acetaminophen. In additional embodiments, the dosage form produces a minimum Cmax for acetaminophen of about 2.0 µg/ml and the maximum Cmax of about 10.4 µg/ml after a single dose of 1000 mg acetaminophen. In preferred embodiments, the dosage form produces a Cmax for acetaminophen of between about 3.0 and 5.2 µg/ml after a single dose of 1000 mg acetaminophen.

In other embodiments, the plasma concentration profile for hydrocodone exhibits an area under the concentration time curve between about 275 and about 562 ng*hr/ml after a single dose of 30 mg hydrocodone bitartrate. In additional embodiments, the plasma concentration profile for hydrocodone exhibits a minimum area under the concentration time curve of about 228 ng*hr/ml and a maximum area under the concentration time curve of about 754 ng*hr/ml after a single dose of 30 mg hydrocodone bitartrate.

In particular embodiments, the plasma concentration profile for acetaminophen exhibits an area under the concentration time curve between about 28.7 and about 57.1 ng*hr/ml after a single dose of 1000 mg acetaminophen. In other embodiments, the plasma concentration profile for acetaminophen exhibits a minimum area under the concentration time curve of about 22.5 ng*hr/ml and a maximum area under the concentration time curve of about 72.2 ng*hr/ml after a single dose of 1000 mg acetaminophen.

In particular embodiments, when administered to the human patient, the plasma concentration for hydrocodone at 12 hours (C12) is between about 11.0 and about 27.4 ng/ml after a single dose of 30 mg hydrocodone bitartrate, and the plasma concentration for acetaminophen at 12 hours (C12) is between about 0.7 and 2.5 µg/ml after a single dose of 1000 mg acetaminophen.

In additional embodiments, the plasma concentration profile exhibits a width at half height value for hydrocodone of between about 6.4 and about 19.6 hours, the plasma concentration profile exhibits a width at half height value for acetaminophen of between about 0.8 and about 12.3 hours.

In particular embodiments, when administered to the human patient, the plasma concentration profile exhibits a weight ratio of acetaminophen to hydrocodone between about 114.2 and 284 at one hour after oral administration of a single dose containing 1000 mg acetaminophen and 30 mg hydrocodone to a human patient. In additional embodiments, the plasma concentration profile exhibits a weight ratio of acetaminophen to hydrocodone between about 70.8 and 165.8 at six hours after oral administration of a single dose containing 1000 mg acetaminophen and 30 mg hydrocodone to a human patient. In yet other embodiments, the plasma concentration profile exhibits a weight ratio of acetaminophen to hydrocodone between about 36.4 and 135.1 at 12 hours after oral administration of a single dose containing 1000 mg acetaminophen and 30 mg hydrocodone to a human patient. As mentioned previously herein, it has been discovered that the sustained release monoeximic dosage forms of the present invention provide analgesia similar to that non-monoeximic dosage forms described by Cruz et al. but are simpler to manufacture in comparison to dosage forms disclosed by Cruz et al.

The monoeximic dosage forms of the present invention can be administered to a human patient in a manner to provide effective concentrations of analgesic to quickly combat existing pain (e.g., within about 1 hour) and provide a sustained release to maintain levels of analgesic agents (namely, one or more opioid analgesics and one or more nonopioid analgesics) sufficient to alleviate pain or minimize the possibility of breakthrough pain for up to about 12 hours after administration of the dosage form.

In a preferred embodiment, the monoeximic dosage form contains about 450 mg to about 550 mg acetaminophen and about 10 mg to about 20 mg hydrocodone bitartrate, and when a patient is administered a dose of two of said monoeximic dosage forms, the dosage form produces a Cmax for hydrocodone of between about 19.4 and 42.8 ng/ml and an mean area under the concentration time curve between about 275 and about 562 ng*hr/ml after a single dose of 30 mg hydrocodone bitartrate, and a Cmax for acetaminophen of between about 3.0 and about 7.9 μg/ml and an mean area under the concentration time curve between about 28.7 and about 57.1 μg*hr/ml after a single dose of 1000 mg acetaminophen.

The monoeximic dosage forms of the present invention preferably provide a $T_{90}$ of between about 5 and about 12 hours, and more preferably of from about 8 to about 10 hours.

The monoeximic dosage form of the present invention may be manufactured by standard techniques known by those skilled in the art. For example, the dosage form can be manufactured using a wet granulation technique. In the wet granulation technique, a drug and the ingredients comprising the drug composition are mixed in a mixer to form a drug blend. Next, other ingredients comprising the drug composition can be optionally dissolved in a portion of the granulation fluid to form a wet blend. The granulation fluid can be in the form of an aqueous solution or can contain one or more solvents. Then, the prepared wet blend is slowly added to the drug blend with continual mixing in the mixer. The granulating fluid is added until wet granules are produced. The wet granules are then optionally forced through a predetermined screen onto oven trays. The blend is dried under suitable conditions, for example, 18 to 24 hours at 24° C. to 60° C. in a forced-air oven. The dried granules are then sized. Next, a suitable lubricant such as magnesium stearate is added to the drug granulation. The powder blend can then be compressed into tablets using a rotary press or a hydraulic press (e.g., Carver press). The speed of the press can be set at 20 rpm and the maximum load set can be set at 2 tons.

Similarly, thermal forming, melt granulation, dry granulation, direct compression, and various other suitable methods and techniques known in the art can be used to make the monoeximic dosage forms of the present invention.

A preferred embodiment of the monoeximic dosage form is a homogeneous monoeximic matrix system.

Another preferred embodiment of the monoeximic dosage form is a monoeximic reservoir system that comprises one or more opioid analgesics such as Hydrocodone, one or more nonopioid analgesics such as acetaminophen and a single rate controlling mechanism. In developing reservoir systems, commonly used methods include microencapsulation of drug particles, film coating of tablets or multiparticulates, and press-coating of tablets.

Another preferred embodiment of the monoeximic dosage form is a monoeximic osmotic system that comprises one or more opioid analgesics such as Hydrocodone, one or more nonopioid analgesics such as acetaminophen and a single rate controlling mechanism. Examples of osmotic systems with similarity to this embodiment of the invention are described in U.S. Pat. Nos. 6,495,162, 6,485,748 to Cheng and Chen, respectively.

As discussed previously herein, the monoeximic dosage forms of the present invention include a single rate controlling mechanism. Additionally, the monoeximic dosage forms of the present invention can also optionally include one or more pharmaceutically acceptable excipients that ease the manufacturing process or improve the performance of the dosage form or both. Common excipients include diluents or bulking agents, lubricants, binders, etc. Such excipients are routinely used in the dosage forms of the present invention.

Diluents, or fillers, are added in order to increase the mass of an individual dose to a size suitable for tablet compression. Suitable diluents include powdered sugar, calcium phosphate, calcium sulfate, microcrystalline cellulose, lactose, mannitol, kaolin, sodium chloride, dry starch, sorbitol, etc.

Lubricants are incorporated into dosage forms for a variety of reasons. For example, they optionally reduce friction between the granulation and die wall during compression and ejection in embodiments that use applicable techniques. This prevents the granulate from sticking to the tablet punches, facilitates its ejection from the tablet punches, etc. Examples of suitable lubricants include talc, stearic acid, vegetable oil, calcium stearate, zinc stearate, magnesium stearate, etc.

Glidants are also typically incorporated into the dosage form. A glidant improves the flow characteristics of the granulation. Examples of suitable glidants include talc, silicon dioxide, and cornstarch.

Surfactants and disintegrants may also be utilized in the carrier as well. Disintegrants generally include starches, clays, celluloses, algins and gums and crosslinked starches, celluloses and polymers. Representative disintegrants include corn starch, potato starch, croscarmellose, crospovidone, sodium starch glycolate, Veegum HV, methylcellulose, agar, bentonite, carboxymethylcellulose, low substituted carboxymethylcellulose, alginic acid, guar gum and the like. A preferred disintegrant is croscarmellose sodium.

Exemplary surfactants are those having an HLB value of between about 10-25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Surfactants that are useful generally include ionic surfactants, including anionic, cationic, and zwitterionic surfactants, and nonionic surfactants. Nonionic surfactants are preferred in certain embodiments and include, for example, polyoxyl stearates such as polyoxyl 40 stearate, polyoxyl 50 stearate, polyoxyl 100 stearate, polyoxyl 12 distearate, polyoxyl 32 distearate, and polyoxyl 150 distearate, and other Myrj™ series of surfactants, or mixtures thereof. Yet another class of surfactant useful in forming the dissolved drug are the triblock co-polymers of ethylene oxide/propylene oxide/ethylene oxide, also known as poloxamers, having the general formula $HO(C_2H_4O)_a(C_3H_6O)_b(C_2H_4O)_aH$, available under the tradenames Pluronic and Poloxamer. In this class of surfactants, the hydrophilic ethylene oxide ends of the surfactant molecule and the hydrophobic midblock of propylene oxide of the surfactant molecule serve to dissolve and suspend the drug. These surfactants are solid at room temperature. Other useful surfactants include sugar ester surfactants, sorbitan fatty acid esters such as sorbitan monolaurate, sorbitan monopalmitate, sorbitan monostearate, sorbitan tristearate, and other Span™ series surfactants, glycerol fatty acid esters such as glycerol monostearate, polyoxyethylene derivatives such as polyoxyethylene ethers of high molecular weight aliphatic alcohols (e.g., Brij 30, 35, 58, 78 and 99) polyoxyethylene stearate (self emulsifying), polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 2 cetyl ether with butylated hydroxyanisole, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, polyoxyethylene derivatives of fatty acid esters of sorbitan such as polyoxyethylene 4 sorbitan monostearate, polyoxyethylene 20 sorbitan tristearate, and other Tween™ series of surfactants, phospholipids and phospholipid fatty acid derivatives such as lecithins, fatty amine oxides, fatty acid alkanolamides, propylene glycol monoesters and monoglycerides, such as hydrogenated palm oil monoglyceride, hydrogenated soybean oil monoglyceride, hydrogenated palm stearine monoglyceride, hydrogenated vegetable monoglyceride, hydrogenated cottonseed oil monoglyceride, refined palm oil monoglyceride, partially hydrogenated soybean oil monoglyceride, cotton seed oil monoglyceride sunflower oil monoglyceride, sunflower oil monoglyceride, canola oil monoglyceride, succinylated monoglycerides, acetylated monoglyceride, acetylated hydrogenated vegetable oil monoglyceride, acetylated hydrogenated coconut oil monoglyceride, acetylated hydrogenated soybean oil monoglyceride, glycerol monostearate, monoglycerides with hydrogenated soybean oil, monoglycerides with hydrogenated palm oil, succinylated monoglycerides and monoglycerides, monoglycerides and rapeseed oil, monoglycerides and cottonseed oils, monoglycerides with propylene glycol monoester sodium stearoyl lactylate silicon dioxide, diglycerides, triglycerides, polyoxyethylene steroidal esters, Triton-X series of surfactants produced from octylphenol polymerized with ethylene oxide, where the number "100" in the trade name is indirectly related to the number of ethylene oxide units in the structure, (e.g., Triton X-100™ has an average of N=9.5 ethylene oxide units per molecule, with an average molecular weight of 625) and having lower and higher mole adducts present in lesser amounts in commercial products, as well as compounds having a similar structure to Triton X-100™, including Igepal CA-630™, and Nonidet P-40M (NP-40™, N-lauroylsarcosine, Sigma Chemical Co., St. Louis, Mo.), and the like. Any of the above surfactants can also include optional added preservatives such as butylated hydroxyanisole and citric acid. In addition, any hydrocarbon chains in the surfactant molecules can be saturated or unsaturated, hydrogenated or unhydrogenated.

A resource of surfactants including solid surfactants and their properties is available in *McCutcheon's Detergents and Emulsifiers*, International Edition 1979 and *McCutcheon's Detergents and Emulsifiers*, North American Edition 1979. Other sources of information on properties of solid surfactants include *BASF Technical Bulletin Pluronic & Tetronic Surfactants* 1999 and *General Characteristics of Surfactants from ICI Americas Bulletin* 0-1 10/80 5M, and Eastman Food Emulsifiers Bulletin ZM-1K October 1993.

Surfactants can be included as a single (one) surfactant or as a blend of surfactants. The surfactants are selected such that they have values that promote the dissolution and solubility of the drug. A high HLB surfactant can be blended with a surfactant of low HLB to achieve a net HLB value that is between them, if a particular drug requires the intermediate HLB value. The surfactant is selected depending upon the drug being delivered; such that the appropriate HLB grade is utilized.

Binders may be incorporated into the monoeximic dosage forms of the present invention. Binders are typically utilized if the manufacture of the dosage form uses a granulation step. Examples of suitable binders include povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Other excipients that may be incorporated into the dosage form include preservatives, antioxidants, or any other excipient commonly used in the pharmaceutical industry, etc. The amount of excipients used in the dosage form will correspond to that typically used in a matrix system. The total amount of excipients, fillers and extenders, etc. varies.

Embodiments employing matrix formulations can be prepared using any suitable technique. For example, they can be prepared by dry blending a polymer, filler, a nonopioid analgesic, hydrocodone, and other excipients followed by granulating the mixture using an appropriate solvent or aqueous solution until proper granulation is obtained. The granulation is done by methods known in the art. The wet granules are dried in a fluid bed dryer, optionally sifted and ground to appropriate size. Lubricating agents are mixed with the dried granulation to obtain the final formulation. The granulation may also be obtained using a melt or dry granulation technique, such as roller compaction or slugging.

A pore former can be used when the monomeric dosage form of the present invention comprises a membrane. Suitable pore formers include water soluble excipients, such as, hydroxypropyl cellulose, hydroxypropylmethyl cellulose, and polyethylene glycol, sodium chloride.

The monoeximic dosage forms of the present invention are preferably administered orally in the form of tablets or capsules. Tablets and capsules can additionally be prepared with coatings that ease swallowing, provide a taste barrier, or have other functions. As mentioned previously herein, the coating may be colored with a pharmaceutically accepted dye, the amount of which can vary significantly without impacting the performance of the monoeximic dosage form of the present invention.

In another aspect, the present invention relates to an SRSR pharmaceutical composition that comprises at least two sustained release subunits that are bound together. The number of sustained release subunits contained in the pharmaceutical composition is not critical. For example, the pharmaceutical composition can contain 2, 3, 4, 5, 6 or more sustained release subunits. The subunits that comprise the pharmaceutical composition preferably comprise the sustained release monoeximic dosage forms described above, but can also comprise monoeximic subunits that do not individually release the opioid (such as Hydrocodone) and the nonopioid (such as acetaminophen) in accordance with the blood plasma profiles disclosed in Cruz et al.—(see Example 4)

In certain embodiments, the SRSR pharmaceutical composition comprises a first sustained release subunit that comprises acetaminophen, Hydrocodone or both acetaminophen and Hydrocodone and a second sustained release subunit that comprises acetaminophen, Hydrocodone or both acetaminophen and Hydrocodone. Preferably, either the first subunit or the second subunit comprises acetaminophen and Hydrocodone. More preferably, both the first subunit and the second subunit each comprise acetaminophen and Hydrocodone.

In certain further embodiments, each of the subunits comprise the same type of dosage form (such as a matrix system, an osmotic system or a reservoir system). In other embodiments, each of the subunits comprise a different type of monoeximic dosage form. Advantageously, the subunits of the SRSR pharmaceutical composition can include a monoeximic matrix system, a monoeximic osmotic system, a monoexmic reservoir system, or any combinations of a monoeximic matrix system, a monoeximic osmotic system and a monoexmic reservoir system, particularly such monoexemic formulations disclosed above in this patent or patent application. For example, the pharmaceutical compositions of the present invention can comprise the following: (1) a first subunit that comprises a monoeximic matrix system and a second subunit that comprises a monoeximic matrix system; (2) a first subunit that comprises a monoeximic osmotic system and a second subunit that comprises a monoeximic osmotic system; (3) a first subunit that comprises a monoeximic reservoir system and a second subunit that comprises a monoeximic reservoir system; (4) a first subunit that comprises a monoeximic matrix system and a second subunit that comprises a monoeximic osmotic system; (5) a first subunit that comprises a monoeximic matrix system and a second subunit that comprises a monoeximic reservoir system; (6) a first subunit that comprises a monoeximic osmotic system and a second subunit that comprises a monoeximic reservoir system; (7) a first subunit that comprises a monoeximic matrix system, a second subunit that comprises a monoeximic osmotic system and a third subunit that comprises a monoeximic matrix system; and (8) a first subunit that comprises a monoeximic matrix system, a second subunit that comprises a monoeximic matrix system and a third subunit that comprises a monoeximic reservoir system.

The order in which the subunits are arranged or included in the pharmaceutical composition is not critical. For example, the subunits can be physically adhered to or contacted with each another using routine techniques in the art, such as by physically compressing two or more subunits together to form a tablet. Alternatively, each of the subunits can be included or contained in a capsule or other vehicle. Specifically, a capsule can be filled with two or more subunits of a pharmaceutical composition. For example, a capsule can be filed with a first subunit that comprises a monoeximic matrix system and a second subunit that comprises a monoeximic osmotic system.

Like the monoeximic dosage forms described above, the SRSR pharmaceutical compositions of the present invention are suitable for twice daily oral dosing to a human patient for providing relief from pain and exhibit a pharmacokinetic profile similar to these dosage forms. Specifically, the SRSR pharmaceutical compositions comprise an amount of one or more opioid analgesics (such as Hydrocodone) and an amount of one or more nonopioid analgesics (such as acetaminophen) that provides relief from pain for at least about 12 hours. The amount of the one or more nonopioid analgesics in the SRSR pharmaceutical compositions can be between about 20 and about 100 times the amount of one or more opioid analgesics by weight. In certain embodiments, the amount of one or more nonopioid analgesics is between about 20 and about 40 times the amount of one or more opioid analgesics by weight. In particular embodiments, the amount of one or more nonopioid analgesics in the pharmaceutical composition is between about 27 and about 34 times the amount of one or more opioid analgesics by weight. In another embodiment, the amount of one or more nonopioid analgesics is between about 45 and about 55 times the amount of one or more opioid analgesics by weight. In a preferred embodiment, the nonopioid analgesic is acetaminophen and the opioid analgesic is hydrocodone or hydrocodone bitartrate. For example, the pharmaceutical composition can contain about 500 mg of acetaminophen and about 15 mg of Hydrocodone or hydrocodone bitartrate. Alternatively, by way of another example, the pharmaceutical composition can contain about 1000 mg of acetaminophen and about 30 mg of Hydrocodone or hydrocodone bitartrate.

When administered to a human patient, in certain embodiments, the pharmaceutical composition of the present invention is adapted to provide a Cmax for hydrocodone of between about 0.6 ng/mL/mg to about 1.4 ng/mL/mg and a Cmax for acetaminophen of between about 2.8 ng/mL/mg and 7.9 ng/mL/mg after a single dose. In certain other embodiments, the pharmaceutical composition produces a minimum Cmax for hydrocodone of about 0.4 ng/mL/mg to a maximum Cmax for hydrocodone of about 1.9 ng/mL/mg and a minimum Cmax for acetaminophen of about 2.0 ng/mL/mg and maximum Cmax for acetaminophen of about 10.4 ng/mL/mg after a single dose. In additional embodiments, the pharmaceutical composition produces a Cmax for hydrocodone of about 0.6 ng/mL/mg to about 1.0 ng/mL/mg and a Cmax for acetaminophen of about 3.0 ng/mL/mg to about 5.2 ng/mL/mg after a single dose.

When administered to the human patient, in certain embodiments, the monoeximic dosage form is adapted to provide a Tmax for hydrocodone of about 1.9 to about 6.7 hours after a single dose. In certain embodiments, the dosage form produces a Tmax for acetaminophen of about 0.5 hours to 6 hours after a single dose, and in other embodiments, the dosage form produces a Tmax for acetaminophen of about 0.9 to about 2.8 hours after a single dose.

In particular embodiments, when administered to the human patient, the SRSR pharmaceutical composition produces an AUC for hydrocodone of between about 9.1 ng*hr/mL/mg to about 19.9 ng*hr/mL/mg and an AUC for acetaminophen of between about 28.6 ng*hr/mL/mg and about 59.1 ng*hr/mL/mg after a single dose. In additional embodiments, the monoeximic dosage form produces a minimum AUC for hydrocodone of about 7.0 ng*hr/mL/mg to a maximum AUC for hydrocodone of about 26.2 ng*hr/mL/mg and a minimum AUC for acetaminophen of about 18.4 ng*hr/mL/mg and maximum AUC for acetaminophen of 79.9 ng*hr/mL/mg after a single dose. In yet other embodiments, the dosage form produces a mean AUC for hydrocodone of about 11.3 ng*hr/mL/mg to about 18.7 ng*hr/mL/mg of hydrocodone bitartrate and a mean AUC for acetaminophen of 28.7 ng*hr/mL/mg to about 53.5 ng*hr/mL/mg after a single dose.

In certain embodiments, the SRSR pharmaceutical composition produces a Cmax for hydrocodone of between about 0.6 ng/mL/mg to about 1.4 ng/mL/mg and a Cmax for acetaminophen of between about 2.8 ng/mL/mg and 7.9 ng/mL/mg, and a mean AUC for hydrocodone of between about 11.3 ng*hr/mL/mg to about 18.7 ng*hr/mL/mg and a mean AUC for acetaminophen of between about 28.7 ng*hr/mL/mg and about 53.5 ng*hr/mL/mg after a single dose.

In yet other embodiments, the SRSR pharmaceutical composition produces a Cmax for hydrocodone of between about 19.6 and 42.8 ng/ml after a single dose of 30 mg hydrocodone, while in other embodiments, the SRSR pharmaceutical composition produces a minimum Cmax for hydrocodone of about 12.7 ng/ml and the maximum Cmax for hydrocodone of about 56.9 ng/mL after a single dose of 30 mg Hydrocodone.

In a preferred embodiment, the SRSR pharmaceutical composition produces a Cmax for hydrocodone of between about 19.6 and 31 ng/ml after a single dose of 30 mg Hydrocodone.

In other embodiments, the pharmaceutical composition produces a Cmax for acetaminophen of between about 3.0 and about 7.9 µg/ml after a single dose of 1000 mg acetaminophen. In additional embodiments, the SRSR pharmaceutical composition produces a minimum Cmax for acetaminophen of about 2.0 µg/ml and the maximum Cmax of about 10.4 µg/ml after a single dose of 1000 mg acetaminophen. In preferred embodiments, the SRSR pharmaceutical composition produces a Cmax for acetaminophen of between about 3.0 and 5.2 µg/ml after a single dose of 1000 mg acetaminophen.

In other embodiments, the plasma concentration profile for hydrocodone exhibits an area under the concentration time curve between about 275 and about 562 ng*hr/ml after a single dose of 30 mg hydrocodone bitartrate. In additional embodiments, the plasma concentration profile for hydrocodone exhibits a minimum area under the concentration time curve of about 228 ng*hr/ml and a maximum area under the concentration time curve of about 754 ng*hr/ml after a single dose of 30 mg hydrocodone bitartrate.

In particular embodiments, the plasma concentration profile for acetaminophen exhibits an area under the concentration time curve between about 28.7 and about 57.1 ng*hr/ml after a single dose of 1000 mg acetaminophen. In other embodiments, the plasma concentration profile for acetaminophen exhibits a minimum area under the concentration time curve of about 22.5 ng*hr/ml and a maximum area under the concentration time curve of about 72.2 ng*hr/ml after a single dose of 1000 mg acetaminophen.

In particular embodiments, when administered to the human patient, the plasma concentration for hydrocodone at 12 hours (C12) is between about 11.0 and about 27.4 ng/ml after a single dose of 30 mg hydrocodone bitartrate, and the plasma concentration for acetaminophen at 12 hours (C12) is between about 0.7 and 2.5 µg/ml after a single dose of 1000 mg acetaminophen.

In additional embodiments, the plasma concentration profile exhibits a width at half height value for hydrocodone of between about 6.4 and about 19.6 hours, the plasma concentration profile exhibits a width at half height value for acetaminophen of between about 0.8 and about 12.3 hours.

In particular embodiments, when administered to the human patient, the plasma concentration profile exhibits a weight ratio of acetaminophen to hydrocodone between about 114.2 and 284 at one hour after oral administration of a single dose containing 1000 mg acetaminophen and 30 mg Hydrocodone to a human patient. In additional embodiments, the plasma concentration profile exhibits a weight ratio of acetaminophen to hydrocodone between about 70.8 and 165.8 at six hours after oral administration of a single dose containing 1000 mg acetaminophen and 30 mg Hydrocodone to a human patient. In yet other embodiments, the plasma concentration profile exhibits a weight ratio of acetaminophen to hydrocodone between about 36.4 and 135.1 at 12 hours after oral administration of a single dose containing 1000 mg acetaminophen and 30 mg hydrocodone to a human patient. The SRSR pharmaceutical compositions of the present invention can be administered to a human patient in a manner to provide effective concentrations of analgesic to quickly combat existing pain (e.g., within about 1 hour) and provide a sustained release to maintain levels of analgesic agents sufficient to alleviate pain or minimize the possibility of breakthrough pain for up to about 12 hours after administration of the dosage form.

In a preferred embodiment, the pharmaceutical composition contains about 450 mg to about 550 mg acetaminophen and about 10 mg to about 20 mg hydrocodone bitartrate, and when a patient is administered a dose of two of said pharmaceutical compositions, the dosage form produces a Cmax for hydrocodone of between about 19.4 and 42.8 ng/ml and an mean area under the concentration time curve between about 275 and about 562 ng*hr/ml after a single dose of 30 mg hydrocodone bitartrate, and a Cmax for acetaminophen of between about 3.0 and about 7.9 µg/ml and an mean area under the concentration time curve between about 28.7 and about 57.1 µg*hr/ml after a single dose of 1000 mg acetaminophen.

The pharmaceutical composition of the present invention preferably provides a $T_{90}$ of between about 5 and about 12 hours, and more preferably of from about 8 to about 10 hours.

In certain embodiments, the SRSR pharmaceutical composition comprises a therapeutically effective amount of the dose of opioid analgesic and nonopioid analgesic that exhibits a release rate in vitro of the opioid analgesic and nonopioid analgesic of from about 19% to about 49% within 0.75 hours, about 25% to about 42% released after 50 minutes, from about 40% to about 65% released after 210 minutes, and about 70% to about 100% released after 480 minutes. In additional embodiments, the pharmaceutical composition comprises a therapeutically effective amount of the dose of opioid analgesic and nonopioid analgesic that exhibits a release rate in vitro of the opioid analgesic and nonopioid analgesic of at least 90% released within about 8 hours. In further additional embodiments, the pharmaceutical composition comprises a therapeutically effective amount of the dose of opioid analgesic and nonopioid analgesic that exhibits a release rate in vitro of the opioid analgesic and nonopioid analgesic of at least 90% released within about 12 hours.

The monoeximic dosage forms and SRSR pharmaceutical compositions described above can be used in a variety of methods. For example, the dosage forms and pharmaceutical compositions can be used in methods for providing an effective concentration of one or more opioid analgesics such as Hydrocodone and one or more nonopioid analgesics such as acetaminophen in the plasma of a human patient for the treatment of pain, methods for treating pain in a human patient, methods for providing sustained release of one or more opioid analgesics and one or more opioid analgesics and methods for providing an effective amount of an analgesic composition for treating pain in a human patient in need thereof, and so forth.

An advantage of the present invention relates to the improved ability to treat pain in a variety of patients with a simpler formulation or composition than the non-monoeximic and complex dosage forms described in Example 4 of Cruz et al. Pain management often involves a combination of a chronic pain medication with a rescue medication.

The sustained release monoeximic dosage forms and pharmaceutical compositions of the present invention provide a means for producing or providing the following plasma profiles in human patients. Any and all of these pharmacokinetic parameters are expressly encompassed within the scope of the invention and the appended claims.

Specifically, when administered to a human patient, in certain embodiments, the dosage form or pharmaceutical composition produces the blood plasma concentration profiles described above.

It is to be understood that while the invention has been described in conjunction with the preferred specific embodiments thereof, that the description above as well as the examples that follow are intended to illustrate and not limit the scope of the invention. The practice of the present invention will employ, unless otherwise indicated, conventional techniques of organic chemistry, polymer chemistry, pharmaceutical formulations, and the like, which are within the skill of the art. Other aspects, advantages and modifications within the scope of the invention will be apparent to those skilled in the art to which the invention pertains. Such techniques are explained fully in the literature.

Example 1

Preparation of Extended Release Monoeximic Dosage Forms Containing Acetaminophen (APAP) and Hydrocodone Bitartrate Hemipentahydrate (HBH) at Lab Scale This example shows the preparation of single unit monoeximic matrix dosage forms.

Tablets weighing about 800 mg were prepared using wet granulation using a laboratory high shear mixer (Key International Inc.). APAP dense powder was dry mixed with HBH, and excipients except for APAP DC-90, silicon dioxide and magnesium stearate for 1.0 minute (150 rpm) followed by granulating with Eudragit L-30D aqueous dispersion at low speed (200 rpm) for approximately 2.0 minutes in the high shear mixer. The wet granules were then dried in an oven at 50° C. overnight and passed through a 20-mesh screen. The granulation was blended with APAP DC-90 and silicon dioxide for 3.0 minutes, and magnesium stearate for an additional 2.0 minutes at 25 rpm in a V-blender. The powder blend was subsequently compressed into tablets using a hydraulic Carver press. Tablet compression force is 1.5 metric Ton; Hardness=18.8 SCU. The dimension of the monolithic SR tablets were about 18×8×6 mm. The batch size of each experimental run was 300 g. Example formulations that were investigated to obtain different release rates are provided in Table 1 below.

Dissolution tests were performed to evaluate dissolution rates of the monoeximic dosage formulations of Table 1 using USP Apparatus II operating at 75 rpm in simulated intestinal fluid (SIF, pH 6.8 phosphate buffer) at 37° C. The dissolution samples were analyzed using a validated high pressure liquid chromatography (HPLC) assay method for both APAP and HBH. Drugs were resolved on a Varian, Polaris, C8 Ether (3 µm Particle Size) and detected by UV absorption (280 nm for APAP and 215 nm for HBH). Standard solutions of each drug were prepared in concentration increments encompassing the range of 72 to 660 µm/mL for APAP and 2.5 to 24 µg/mL for HBH and analyzed by HPLC. Standard curves were constructed using linear regression analysis of peak areas versus concentration for APAP and HBH respectively. Quantitation of sample concentrations were performed based on peak areas using standard curves. The results are provided in Table 2 and in FIG. 1. The in vitro studies demonstrated that the monoeximic dosage formulations of Table 1 produced (1) a range of biphasic extended release profiles with a different percentage (%) of immediate release of APAP and HBHHBH, and (2) similar release rates of APAP and HBH can be obtained despite the higher solubility of HBH. The reference is the 8-hr osmotic pump system described in Example 4 of Cruz et al. (U.S. Patent Publication No. 20050158382).

TABLE 1

Composition (%) of single unit monoeximic extended release tablets containing APAP and HBH

| | Formulation | | |
|---|---|---|---|
| | A | B | C |
| | | Label | |
| Ingredients | SR1 | SR3 | Mix8 |
| APAP Dense Powder, | 65.3 | 65.3 | 18.8 |
| APAP DC-90 fine (extra-granular) | — | — | 48.6 |
| HBH | 1.9 | 1.9 | 1.9 |
| HPMC, Methocel K100LV | — | 17.5 | 23.8 |
| HPMC, Methocel K4M | 17.5 | — | — |
| Eudragit L-30D-55 -dry weight- | 2.4 | 2.4 | 4.0 |
| Avicel PH101 | 11.0 | — | — |
| Dicalcium Phosphate | — | 11.0 | — |
| HPC, Klucel EXF | 1.0 | 1.0 | 2.0 |
| Magnesium Stearate | 0.5 | 0.5 | 0.5 |
| Silicon dioxide | 0.5 | 0.5 | 0.5 |
| Tablet weight (mg) | 800 | 800 | 800 |

TABLE 2

In vitro dissolution of APAP and HBH from single unit monoeximic extended release tablets

| | Time (hr) | | | | | | | | | |
|---|---|---|---|---|---|---|---|---|---|---|
| | 1 | 2 | 3 | 4 | 5 | 6 | 7 | 8 | 9 | 10 |
| Monoeximic tablet Formulation A | | | | | | | | | | |
| APAP | 30.5 | 41.1 | 49.1 | 55.6 | 61.3 | 66.1 | 70.3 | 74.0 | 77.3 | 80.5 |
| HBH | 42.6 | 56.9 | 64.5 | 70.4 | 75.2 | 79.5 | 83.2 | 86.5 | 89.5 | 92.2 |
| Formulation B | | | | | | | | | | |
| APAP | 46.3 | 61.2 | 72.1 | 80.3 | 86.9 | 92.3 | 97.6 | 101.7 | 104.9 | 107.8 |
| HBH | 50.2 | 63.6 | 73.5 | 80.8 | 86.8 | 95.6 | 97.1 | 98.7 | 101.7 | 103.4 |
| Formulation C | | | | | | | | | | |
| APAP | 28.9 | 39.4 | 48.5 | 56.2 | 63.0 | 69.2 | 74.7 | 80.1 | 85.0 | 89.3 |
| HBH | 33.1 | 45.6 | 54.7 | 62.0 | 68.3 | 73.5 | 78.0 | 82.4 | 86.4 | 90.0 |

TABLE 2-continued

In vitro dissolution of APAP and HBH from single unit monoeximic extended release tablets

|  | Time (hr) | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Reference (Example 4 of Cruz, et al.) | | | | | | | | | | |
| APAP | 36 | 42 | 49 | 57 | 66 | 76 | 89 | 99 | 102 | 102 |
| HBH | 36 | 42 | 51 | 61 | 73 | 83 | 95 | 102 | 105 | 105 |

Example 2

Preparation of Sustained Release Monoeximic Dosage Forms Containing APAP and HBH at Lab Scale This following example shows the preparation of multi-unit monoeximic matrix dosage forms.

Tablets weighing 192-200 mg were each prepared using wet granulation or direct compression. For wet granulation, APAP dense powder was dry mixed with HBH, lactose and proportional amount of hydroxypropyl methylcellulose (HPMC) (listed in Table 3 below as Methocel K100LV and Methocel K4M) for 2-3 minutes (150 rpm) followed by granulation with an Eudragit L-30D aqueous dispersion at low speed (200 rpm) for approximately 2 minutes in a laboratory high shear mixer (Key International Inc.). The wet granules were then dried in an oven at 50° C. overnight and passed through a 20-mesh screen. The granulation was blended with other excipients including the remainder of HPMC, hydroxylpropyl cellulose (HPC) (listed in Table 3 below as Kluecel EXF), APAP DC-90 and silicon dioxide for 3 minutes and then with the magnesium stearate for an additional 2 minutes at 25 rpm in a V-blender. For direct compression, all of the active agents (APAP and HBH) and excipients except for magnesium stearate were mixed for 3 minutes followed by blending with magnesium stearate for an additional 2 minutes at 25 rpm in a V-blender. The powder blend was subsequently compressed into tablets using a hydraulic Carver press or a rotary press. The diameter of the tablets were about 7.13 mm.

The batch size of Blend 16 (Formulation D), Blend 18 (Formulation E), Mix 11 (Formulation J), Mix 12 (Formulation K) and Mix 13 (Formulation L), Mix 14 (Formulation M), Mix 15 (Formulation N), and Mix 16 (Formulation O) is between about 350 g to about 500 g. The final dosage form was obtained by filling 4 tablets into a Size 00 capsule for dissolution testing. The various formulations were studied to obtain different release rates. Example formulations are provided in Table 3. Other rate controlling polymers tested included Kollidon SR (polyvinyl acetate/polyvinylpyrrolidone).

Dissolution tests were performed to evaluate dissolution rates of the monoeximic dosage formulations of Table using the same method described in Example 1. The in vitro studies demonstrated that the monoeximic dosage formulations of Table 3 produced (1) a range of biphasic extended release profiles with a different percentage (%) of immediate release of APAP and HBH; and (2) similar release rates of APAP and HBH despite the higher solubility of HBH. The reference is the 8-hr osmotic pump system described in Example 4 of Cruz et al. (U.S. Patent Publication No. 20050158382).

TABLE 3

Composition (%) of multi-unit monoeximic extended release tablets containing APAP and HBH

| | Formulation | | | | |
| --- | --- | --- | --- | --- | --- |
| | D | E | G | H | I |
| | | | Label | | |
| Ingredients | Blend 16 | Blend 18 | Mix 8 | Mix 9 | Mix 10 |
| APAP Dense Powder, Intragranular | — | — | 18.8 | 19.5 | 18.8 |
| APAP DC-90 fine | 69.5 | 69.5 | 48.6 | 50.5 | 48.6 |
| HBH | 1.9 | 1.9 | 1.9 | 1.9 | 1.9 |
| HPMC, Methocel K100LV | 25.7 | — | 23.8 | 20.85 | 0 |
| HPMC, Methocel K4M | — | 23.7 | — | — | 23.8 |
| Carbopol 974P | 2.0 | 4.0 | — | — | 0 |
| Eudragit L-30D-55- dry weight- | — | — | 4 | 4.0 | 4.0 |
| Lactose monohydrate | — | — | — | — | — |
| HPC, Klucel EXF | — | — | 2.0 | 2.2 | 2.0 |
| Magnesium Stearate | 0.5 | 0.5 | 0.5 | 0.5 | 0.5 |
| Silicon dioxide | 0.5 | 0.5 | 0.5 | 0.5 | 0.5 |
| Tablet weight (mg) | 800 | 800 | 800 | 770 | 800 |

| | Formulation | | | | | |
| --- | --- | --- | --- | --- | --- | --- |
| | J | K | L | M | N | O |
| | | | Label | | | |
| Ingredients | Mix 11 | Mix 12 | Mix 13 | Mix 14 | Mix 15 | Mix 16 |
| APAP Dense Powder, Intragranular | 19.5 | 12.5 | 18.8 | 19.5 | 18.8 | 18.8 |
| APAP DC-90 fine | 50.5 | 55.6 | 48.6 | 50.5 | 48.6 | 48.6 |
| HBH | 1.9 | 1.9 | 1.9 | 1.9 | 1.9 | 1.9 |
| Methocel K100LV | 15.6 | 20.0 | — | 18.0 | 20.0 | — |
| Methocel K4M | — | — | 20.0 | — | — | 20.0 |
| Eudragit L-30D | 2.1 | 4.0 | 4.0 | 2.0 | 2.0 | 4.0 |
| Lactose monohydrate | 6.2 | 3.1 | 3.8 | 3.0 | 3.0 | 0 |
| Klucel EXF | 3.1 | 2.0 | 2.0 | 4.0 | 4.8 | 5.8 |
| Magnesium Stearate | 0.5 | 0.5 | 0.5 | 0.5 | 0.5 | 0.5 |
| Silicon dioxide | 0.5 | 0.5 | 0.5 | 0.5 | 0.5 | 0.5 |
| Tablet weight (mg) | 770 | 800 | 800 | 770 | 800 | 800 |

* Composition of APAP DC-90 fine: 90% Acetaminophen, 7.0% Starch, 0.7% Povidone, 1.8% Croscramellose and 0.5% Stearic Acid

TABLE 4

In vitro dissolution of APAP and HBH from multi-unit monoeximic extended release tablets

| | Time (hr) | | | | | | | | | |
|---|---|---|---|---|---|---|---|---|---|---|
| | 1 | 2 | 3 | 4 | 5 | 6 | 7 | 8 | 9 | 10 |
| Formulation D | | | | | | | | | | |
| APAP | 19.1 | 29.1 | 37.1 | 44.0 | 50.4 | 56.4 | 61.9 | 67.0 | 71.7 | 76.1 |
| HBH | 25.6 | 39.4 | 49.3 | 57.4 | 64.4 | 70.7 | 76.0 | 80.7 | 84.9 | 88.6 |
| Formulation E | | | | | | | | | | |
| APAP | 13.4 | 21.8 | 28.3 | 34.2 | 39.5 | 44.4 | 48.9 | 53.3 | 57.3 | 61.0 |
| HBH | 21.0 | 32.9 | 41.4 | 48.6 | 54.7 | 60.1 | 65.1 | 69.6 | 73.4 | 76.9 |
| Formulation G | | | | | | | | | | |
| APAP | 26.7 | 41.8 | 53.8 | 63.5 | 71.4 | 79.2 | 85.2 | 91 | 95.3 | 98 |
| HBH | 29.8 | 44.6 | 54.5 | 63.9 | 71.3 | 77.1 | 81.7 | 85.9 | 89 | 90.7 |
| Formulation H | | | | | | | | | | |
| APAP | 31.3 | 44.8 | 55 | 63.5 | 70.1 | 75.9 | 81 | 85.5 | 89.3 | 92.7 |
| HBH | 31.3 | 45.3 | 54.6 | 61.7 | 67.4 | 72 | 76.3 | 79.6 | 82.2 | 84.5 |
| Formulation I | | | | | | | | | | |
| APAP | 27.5 | 37.3 | 45 | 51.5 | 57.2 | 62.2 | 66.7 | 70.8 | 74.4 | 77.7 |
| HBH | 27.3 | 39.5 | 48.2 | 55.1 | 60.6 | 65.2 | 69.4 | 73.1 | 76.2 | 78.8 |
| Formulation J | | | | | | | | | | |
| APAP | 46.2 | 58.3 | 67.0 | 74.0 | 80.0 | 85.3 | 90.0 | 93.5 | 96.1 | 97.7 |
| HBH | 47.0 | 60.7 | 69.2 | 75.4 | 80.2 | 83.8 | 86.4 | 88.1 | 89.0 | 89.6 |
| Formulation K | | | | | | | | | | |
| APAP | 54.8 | 66.8 | 74.7 | 81.3 | 86.8 | 91.6 | 96.1 | 99.6 | 102.3 | 104.1 |
| HBH | 52.8 | 65.7 | 72.8 | 78.1 | 82.0 | 85.3 | 87.9 | 89.7 | 91.0 | 91.8 |
| Formulation L | | | | | | | | | | |
| APAP | 39.7 | 49.8 | 57.2 | 63.4 | 68.9 | 73.2 | 77.3 | 80.9 | 84.1 | 87.1 |
| HBH | 41.8 | 56.8 | 65.8 | 72.4 | 77.6 | 81.6 | 85.0 | 87.9 | 90.2 | 92.4 |
| Formulation M | | | | | | | | | | |
| APAP | 36.7 | 49.6 | 58.9 | 66.5 | 72.9 | 78.5 | 83.6 | 88.3 | 92.3 | 95.1 |
| HBH | 40.1 | 54.6 | 64.0 | 71.3 | 76.9 | 81.5 | 85.3 | 88.5 | 90.9 | 92.1 |
| Formulation N | | | | | | | | | | |
| APAP | 32.8 | 45.4 | 55.2 | 63.3 | 70.3 | 76.4 | 81.7 | 86.5 | 91.1 | 95.2 |
| HBH | 34.0 | 48.8 | 59.3 | 67.5 | 74.3 | 80.0 | 84.6 | 88.7 | 92.2 | 95.1 |
| Formulation O | | | | | | | | | | |
| APAP | 31.7 | 42.9 | 51.2 | 57.9 | 63.3 | 68.6 | 73.1 | 77.0 | 80.4 | 83.5 |
| HBH | 36.2 | 50.6 | 59.8 | 66.6 | 72.2 | 76.8 | 80.6 | 83.7 | 86.3 | 88.6 |
| Example 4 of Cruz, et al. | | | | | | | | | | |
| APAP | 36 | 42 | 49 | 57 | 66 | 76 | 89 | 99 | 102 | 102 |
| HBH | 36 | 42 | 51 | 61 | 73 | 83 | 95 | 102 | 105 | 105 |

Example 3

Preparation of Extended Release Monoeximic Dosage Forms Containing APAP and HBH at Pilot Plant Scale This example shows (1) multi-unit monoeximic matrix dosage forms designed for bioavailibility evaluations in humans; and (2) the resistance of the monoeximic matrix dosage forms to dose dumping from these dosage forms after the consumption of alcoholic beverages.

The dosage form used in this Example to evaluate human bioavailability and that used to assess the impact of alchoholic solutions on the dosage forms differed from each other by 1% Eudragit L-30D-55 by weight.

Three (3) formulations that were designed for the bioavailability study in healthy subjects are provided in Table 5 below. Tablets weighing about 192.5-200 mg each were prepared using wet granulation. APAP dense powder was dry mixed with HBH, lactose (for Formulation F only) and approximately 8% hydroxypropyl methylcellulose (HPMC, Methocel K100 LV for Formulations F and T, Methocel K4M for Formulations S) for 0.5 minutes (Impeller speed 800 rpm, chopper speed 450 rpm) followed by granulating with Eudragit L-30D-55 aqueous dispersion for approximately 4.5 minutes in a high shear granulator (impeller speed 800 rpm, chopper speed 2000 rpm). The wet granules were passed through a 2.8 mm screen and then dried in an oven at 60° C. The dry granules were passed through a 0.8 mm mesh screen using an oscillator mill. The granules were blended with the other excipients including the remainder of HPMC, hydroxypropyl cellulose (HPC), APAP DC-90, silicon dioxide and magnesium stearate for 1.5 minutes at 30 rpm in a bin-blender. The powder blend was compressed into tablets using a rotary press Korsch XL 100. The diameter of the tablet was about 7 mm. The batch sizes were about 1800 g, about 2100 g and about 2000 g for Formulations F, T and S, respectively. The final dosage form was obtained by filling 4 tablets into a Size 000 capsule for dissolution tests.

Figure 2:
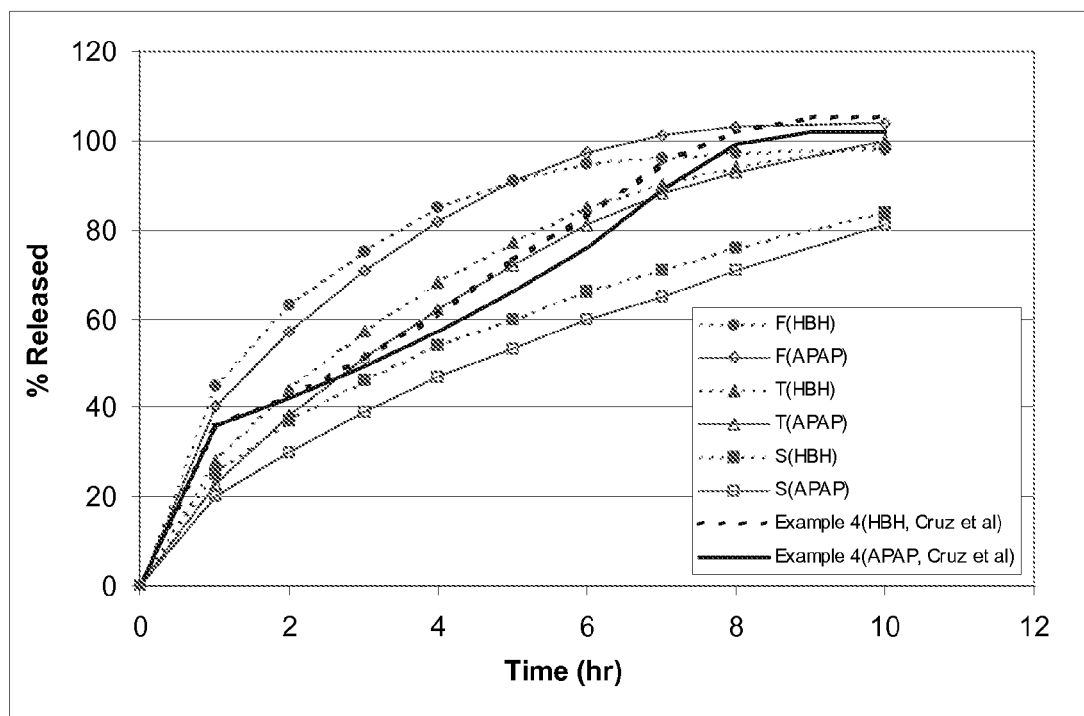
FIG. 2 shows the in vitro drug release of multi-unit monoeximic extended release tablets containing APAP and HBH based on the data shown in Table 6 in Example 3.

Dissolution tests were performed to evaluate dissolution rates of the monoeximic dosage formulations of Table 5 using the same method as described in Example 1. The in vitro results provided in Table 6 below demonstrated that the monoeximic dosage formulations produced a range of biphasic extended release profiles with a range of immediate release and extended release profiles that bracket the release profile of the reference, i.e., 8-hr osmotic pump system described in Example 4 of Cruz et al. (U.S. Patent Publication No. 20050158382). The in vitro data are compared with the reference in FIG. 2.

Additionally, a further study was carried out to determine whether this type of formulation exhibited a more rapid drug release rate in the presence of ethanol. The objective of this study was to assess the effect of concomitant consumption of alcoholic beverages on the potential for dose dumping since APAP and primary rate-controlling polymer, HPMC, are both more soluble in alcohol or alcoholic solutions than in water.

Figure 3:
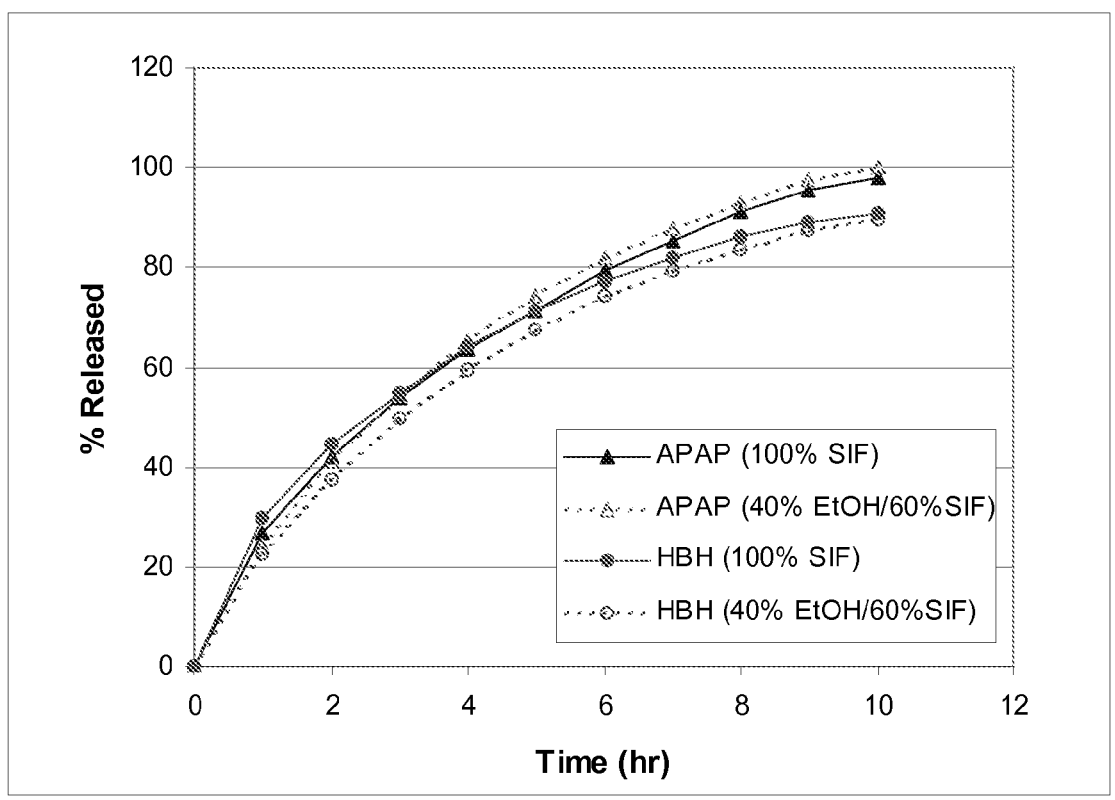
FIG. 3 shows the in vitro drug release of a multi-unit monoeximic extended release tablet (Formulation Te) containing APAP and HBH in simulated intestinal fluid ("SIF") and SIF containing 40% ethanol.

Dissolution tests were performed on Formulation Te (See Table 5), using USP Apparatus II operating at 75 rpm in (i) medium A—0.05 M Phosphate Buffer, pH=6.8; and (ii) medium B—40% ethanol/60% 0.05 M Phosphate Buffer pH 6.8. The results, which are shown in Table 7 below and FIG. 3, indicate that the drug release remains unchanged in SIF containing 40% ethanol, i.e., the single rate controlling mechanism can serve to mitigating the risks of ethanol induced dose dumping of opioid analgesic, such as, HBH.

TABLE 5

Composition (%) of multi-unit monoeximic extended release tablets containing APAP and HBH

|  | Formulation | | | |
|---|---|---|---|---|
|  | F | T | S |  |
|  |  | Label |  |  |
| Ingredients | Fast | Target | Slow | Te |
| APAP Dense Powder, Intragranular | 19.48 | 18.80 | 18.80 | 18.80 |
| APAP DC-90 fine* | 50.51 | 48.6 | 48.6 | 48.60 |
| HBH | 1.95 | 1.88 | 1.88 | 1.88 |
| HPMC, Methocel K100 LV | 15.59 | 23.8 | 6.00 | 23.80 |
| HPMC, Methocel K 4M | — | — | 17.70 | — |
| Eudragit L-30D-55 (-dry weight-) | 2.08 | 3.00 | 3.40 | 4.00 |
| Lactose monohydrate | 6.3 | — | — | — |
| HPC, Klucel EXF | 3.09 | 2.97 | 2.63 | 1.97 |
| Magnesium Stearate | 0.25 | 0.25 | 0.25 | 0.5 |
| Silicon dioxide | 0.75 | 0.75 | 0.75 | 0.5 |
| Tablet weight (mg) | 770 | 800 | 800 | 800 |

*Composition of APAP DC-90 fine: 90% Acetaminophen, 7.0% Starch, 0.7% Povidone, 1.8% Croscramellose and 0.5% Stearic Acid

TABLE 6

In vitro dissolution of multi-unit monoeximic extended release tablets containing APAP and HBH

|  | Time (hr) | | | | | | | | |
|---|---|---|---|---|---|---|---|---|---|
|  | 1 | 2 | 3 | 4 | 5 | 6 | 7 | 8 | 10 |
| Formulation F | | | | | | | | | |
| APAP | 40 | 57 | 71 | 82 | 91 | 97 | 101 | 103 | 104 |
| HBH | 45 | 63 | 75 | 85 | 91 | 95 | 96 | 97 | 98 |
| Formulation T | | | | | | | | | |
| APAP | 23 | 38 | 51 | 62 | 72 | 81 | 88 | 93 | 100 |
| HBH | 28 | 44 | 57 | 68 | 77 | 85 | 90 | 94 | 99 |
| Formulation S | | | | | | | | | |
| APAP | 20 | 30 | 39 | 47 | 53 | 60 | 65 | 71 | 81 |
| HBH | 25 | 37 | 46 | 54 | 60 | 66 | 71 | 76 | 84 |
| Reference (Example 4 of Cruz, et al.) | | | | | | | | | |
| APAP | 36 | 42 | 49 | 57 | 66 | 76 | 89 | 99 | 102 |
| HBH | 36 | 42 | 51 | 61 | 73 | 83 | 95 | 102 | 105 |

TABLE 7

In vitro dissolution of a multi-unit monoeximic extended release tablet (Te) containing APAP and HBH in the presence of ethanol (n = 3)

|  | Time (hr) | | | | | | | | | |
|---|---|---|---|---|---|---|---|---|---|---|
|  | 1 | 2 | 3 | 4 | 5 | 6 | 7 | 8 | 9 | 10 |
| In SIF | | | | | | | | | | |
| APAP | 26.7 | 41.8 | 53.8 | 63.5 | 71.4 | 79.2 | 85.2 | 91.0 | 95.3 | 98.0 |
| SD | 2.5 | 2.9 | 2.6 | 2.4 | 1.5 | 1.6 | 1.7 | 2.1 | 1.9 | 1.3 |
| HBH | 29.8 | 44.6 | 54.5 | 63.9 | 71.3 | 77.1 | 81.7 | 85.9 | 89.0 | 90.7 |
| SD | 2.6 | 2.6 | 3.9 | 2.2 | 1.7 | 1.7 | 1.6 | 1.6 | 1.7 | 1.3 |
| In 40% EtOH/60% SIF | | | | | | | | | | |
| APAP | 24.2 | 41.0 | 54.4 | 65.1 | 74.2 | 81.8 | 87.8 | 92.8 | 97.4 | 100.2 |
| SD | 1.6 | 1.8 | 1.8 | 2.4 | 2.7 | 3.3 | 3.2 | 3.1 | 3.1 | 3.2 |
| HBH | 22.4 | 37.4 | 49.5 | 59.3 | 67.5 | 74.1 | 79.3 | 83.5 | 87.3 | 89.6 |
| SD | 0.4 | 0.1 | 0.3 | 0.1 | 0.6 | 1.1 | 1.0 | 0.8 | 0.5 | 0.6 |

Example 4

Preparation of Extended Release Monoeximic Dosage Forms Containing APAP and HBH at Lab Scale This example shows the preparation of multi-unit monoeximic reservoir dosage forms.

Tablets weighing 200 mg were prepared using wet granulation. APAP dense powder was dry mixed with HBH, lactose and SDS for 1.0 minutes (150 rpm) followed by granulation with an Eudragit L-30D aqueous dispersion at low speed (200 rpm) for approximately 1.5 minutes in a laboratory high shear mixer (Key International Inc.). The wet granules were then dried in an oven at 50° C. overnight and passed through a 20-mesh screen. The granulation was blended with hydroxylpropyl cellulose (HPC) and silicon dioxide for 3.0 minutes and then with the magnesium stearate for an additional 2.0 minutes at 25 rpm in a V-blender. The powder blend was subsequently compressed into tablets using a hydraulic Carver press. The diameter of the tablets was about 4.40 mm. The granulation batch size was about 150 g.

To control the release of both APAP and HBH, the tablets were coated in a laboratory coating pan having a diameter of 20.3 cm. The membrane coating solution was prepared by dissolving ethylcellulose (EC), HPC and triethyl citrate (TEC) using acetone as a solvent. The tablets were loaded in the coating pan rotating at 60 rpm and sprayed with the coating solution with a solid content of 18% using a sprang gun until the tablet weight gain reached 5%. The final dosage form was obtained by filling 4 coated tablets into a Size 00 capsule for dissolution testing. Different formulations were studied to obtain different release rates. An example formulation and corresponding dissolution data are provided in Tables 8 and 9. Dissolution tests were performed using the same method described in Example 1. The results showed that the monoeximic dosage formulation produced an overall release rates similar to those of the 8-hr osmotic pump system described in Example 4 of Cruz et al. (U.S. Patent Publication No. 20050158382).

TABLE 8

Composition (%) of multi-unit monoeximic SR extended release tablets containing APAP and HBH

| Core Tablet | % (w/w) |
| --- | --- |
| APAP Dense Powder, Intragranular | 62.5 |
| HBH | 1.9 |
| Eudragit L-30D-55 -dry weight- | 4.5 |
| Lactose monohydrate | 25.1 |
| HPC, Klucel EXF | 2.0 |
| Sodium Dodecyl sulphate (SDS) | 2.0 |
| Silicon dioxide | 1.0 |
| Magnesium Stearate | 1.0 |
| Tablet weight (mg) | 200 mg |
| Membrane Coating | % (w/w) |
| Ethylcellulose | 38.9 |
| HPC, Klucel EXF | 44.4 |
| Triethyl citrate | 16.7 |
| Coating Weight | 10 mg (5% gain) |

TABLE 9

In vitro dissolution of APAP and HBH from Monoeximic extended release tablets of Example 4

| | Time (hr) | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| APAP | 11 | 24 | 39 | 54 | 66 | 75 | 81 | 87 | 92 | 96 |
| HBH | 17 | 34 | 50 | 67 | 81 | 89 | 94 | 97 | 99 | 100 |
| Reference (Example 4 of Cruz, et al.) | | | | | | | | | | |
| APAP | 36 | 42 | 49 | 57 | 66 | 76 | 89 | 99 | — | 102 |
| HBH | 36 | 42 | 51 | 61 | 73 | 83 | 95 | 102 | — | 105 |

Example 5

In Vivo Study in an Animal Model

This following example shows the in vivo bioavailability of a monoeximic matrix dosage form in a minipig model.

In vivo bioavailability of the current invention, Formulation T of Example 3, was assessed in a study using Vicodin CR, a non-monoeximic osmotic pump tablet as a reference, in a group of six minipigs. The dosing interval between formulations was one week. The non-monexmimic reference tablet, Vicodin CR, was prepared based on Examples 2-3 of Cruz et al. (U.S. Patent Publication No. 20050158382). The composition and corresponding dissolution data are provided in Tables 10 and 11, respectively.

Male Göttingen Minipigs (11-15 kg; Ellegard, Denmark) used in the study were fasted overnight prior to dosing but were permitted water ad libitum. Food was allowed about twelve hours post-dosing. Minipigs were housed individually in pens during the studies. For oral administration of the solid dosage form a balling gun was used followed by 50 mL of water. Before the dose administration a blood sample was taken from each animal. Blood samples were withdrawn from the vena jugularis of each animal at approximately 0, 0.5, 1.0, 1.5, 2, 3, 4, 6, 8, 12, 24, 32, 48 and 72 hours after drug administration. Upon collection, the samples were centrifuged at about 4° C. The plasma samples were assayed for acetaminophen and hydrocodone using a liquid chromatography—mass spectrometry method. However, the concentrations of hydrocodone in most samples were below limit of quantitation (LOQ), suggesting rapid metabolism specific to the minipig.

Figure 4:
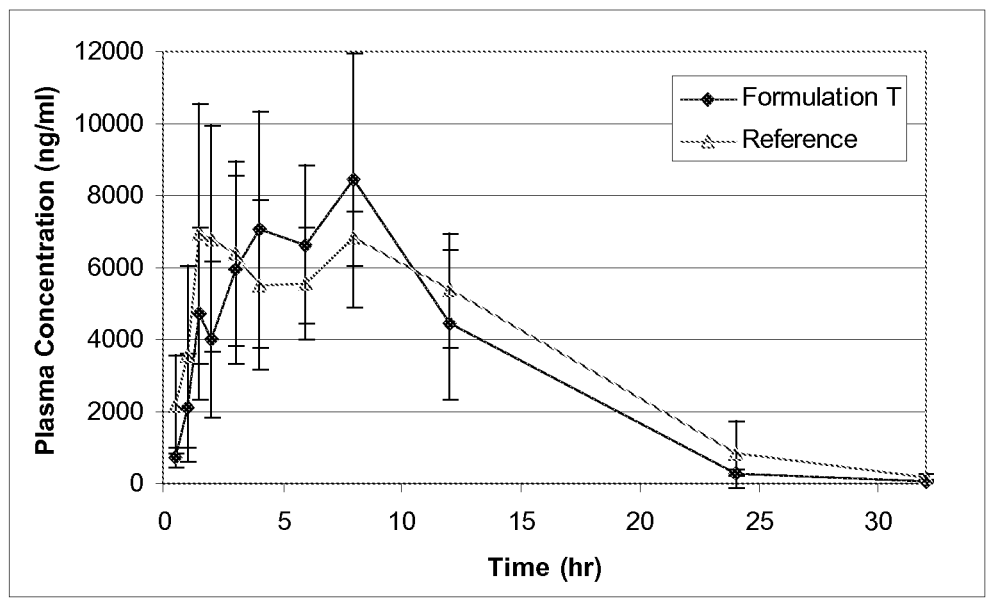
FIG. 4 shows the in vivo plasma profiles of APAP following single oral administration a multi-unit monoeximic extended release tablet (Formulation T from Example 3) containing APAP and HBH in a minipig model.

Results of the bioavailability study are provided in Table 12 and shown in FIG. 4. It was demonstrated that the current invention provides an extended release in vivo pharmacokinetic profile of acetaminophen similar to that of the reference.

TABLE 10

Composition Of The Reference Vicodin CR, A Non-monoeximic Osmotic Pump containing APAP and HBH

| Raw Material Description | Target % (wt/wt) |
| --- | --- |
| Push Layer (138 mg) | |
| Polyethylene Oxide, NF, 303, 7000K, TG, LEO | 61.30 |
| Sodium Chloride, USP, Ph Eur, (Powder) | 30.00 |
| Povidone, USP, Ph Eur, (K29-32) | 5.00 |
| Ferric Oxide, NF, Red | 0.40 |
| Stearic Acid, NF, Powder | 0.25 |
| BHT, FCC, Ph Eur, (Milled) | 0.05 |
| Hydroxypropyl Cellulose, NF, Ph Eur, JP, EXF Pharm | 3.00 |

TABLE 10-continued

Composition Of The Reference Vicodin CR, A Non-monoeximic Osmotic Pump containing APAP and HBH

| Raw Material Description | Target % (wt/wt) |
|---|---|
| Drug Layer (413 mg) | |
| Acetaminophen, USP, Pulverized Dense | 78.56 |
| Hydrocodone Bitartrate, USP (From Athens, GA) | 2.38 |
| Poloxamer 188, NF, Ph Eur (Microprilled) | 8.00 |
| Croscarmellose Sodium, NF | 3.00 |
| Povidone, USP, Ph Eur, (K29-32) | 3.00 |
| Stearic Acid, NF, Powder | 1.50 |
| Magnesium Stearate, NF, Ph Eur | 0.50 |
| BHT, FCC, Ph Eur, (Milled) | 0.01 |
| Hydroxypropyl Cellulose, NF, Ph Eur, JP, EXF Pharm | 2.55 |
| Colloidal Silicon Dioxide, NF | 0.50 |
| Subcoating (10 mg) | |
| Hydroxyethyl Cellulose, NF, Ph Eur, 250 LPH | 7.60 |
| Polyethylene Glycol 3350, NF, LEO | 0.40 |
| Purified Water, USP, Ph Eur* | 92.00 |
| Membrane Coating (64 mg) | |
| Cellulose Acetate, NF, (398-10) | 3.85 |
| Poloxamer 188, NF | 1.15 |
| BHT, FCC, Ph Eur, (Milled) | NA |
| Acetone, NF, (Bulk)/Acetone, NF* | 94.52 |
| Purified Water, USP, Ph Eur* | 0.48 |
| Drug Overcoat (196 mg) | |
| Acetaminophen, USP, (Micronized) | 22.5 |
| Hydrocodone Bitartrate, USP (From Athens, GA) | 0.64 |
| Copovidone, NF | 0.64 |
| HPMC 2910, USP, Ph Eur, 5 cps | 0.97 |
| Hydroxypropyl Cellulose, MF, NF | 0.25 |
| Purified Water, USP, Ph Eur* | 75.00 |
| Color Overcoat (15 mg) | |
| OPADRY, White (YS-2-7063) | 10.00 |
| Purified Water, USP, Ph Eur* | 90.00 |
| Carnauba Wax, NF, Ph Eur, (Powder) | Trace |

*Removed during processing

TABLE 11

In Vitro Dissolution of The Reference Vicodin CR, A Non-monoeximic Osmotic Pump (Lot 18-228-4P)

| | Time (hr) | | | | | | | | | |
|---|---|---|---|---|---|---|---|---|---|---|
| | 1 | 2 | 3 | 4 | 5 | 6 | 7 | 8 | 9 | 10 |
| APAP | 33.7 | 40.6 | 47.8 | 55.8 | 63.7 | 72.8 | 81.0 | 89.5 | 95.8 | 97.5 |
| HBH | 33.2 | 39.1 | 46.1 | 54.3 | 61.7 | 71.0 | 80.5 | 90.2 | 95.7 | 97.2 |

TABLE 12

Summary of Bioavailability Parameters of Acetaminophen Following Oral Administration of Formulation T of Example 3 and Vicodin CR in Minipig Model (Mean, SEM, n = 6)

| Formulation | Cmax (ng/ml) | AUC (ng · hr/ml) | Tmax (hr) | T½ (hr) |
|---|---|---|---|---|
| Reference | 8508 (2324) | 110000 (21100) | 4.2 (3) | 3.5 (0.2) |
| Formulation T | 10319 (3003) | 102000 (20500) | 5.3 (2.3) | 3.3 (0.1) |

Example 6

In Vivo Bioavailability Study in Humans

This example shows the in vivo bioavailability of monoeximic matrix dosage forms in humans.

The clinical lots of monoeximic systems of the present invention, Formulations F, T and S of Example 3, were prepared in a GMP pilot plant for evaluation in a bioavailability study using a non-monoexmimic osmotic pump tablet (Vicodin CR) described in Example 5, as a reference. The in vitro dissolution data of the studied formulations are provided in Table 13, below.

TABLE 13

In vitro dissolution of clinical lots of multi-unit monoeximic SR tablets and the reference studied in a single-dose bioavailability study in healthy volunteers

| | Time (hr) | | | | | | | | |
|---|---|---|---|---|---|---|---|---|---|
| | 1 | 2 | 3 | 4 | 5 | 6 | 7 | 8 | 10 |
| Formulation F (Lot#06-007297) | | | | | | | | | |
| APAP | 46 | 62 | 75 | 86 | 94 | 99 | 102 | 103 | 103 |
| HBH | 53 | 71 | 83 | 91 | 97 | 100 | 101 | 101 | 101 |
| Formulation T (Lot#06-007296) | | | | | | | | | |
| APAP | 21 | 34 | 45 | 54 | 62 | 69 | 76 | 82 | 90 |
| HBH | 27 | 41 | 52 | 62 | 69 | 76 | 82 | 86 | 93 |
| Formulation S (Lot#06-007295) | | | | | | | | | |
| APAP | 20 | 30 | 39 | 46 | 53 | 59 | 64 | 70 | 79 |
| HBH | 26 | 38 | 48 | 55 | 62 | 68 | 73 | 78 | 86 |
| Vicodin CR (Reference; Lot # 06-005903) | | | | | | | | | |
| APAP | 35.0 | 43.0 | 50.9 | 59.1 | 66.5 | 74.5 | 82.1 | 89.7 | 101.8 |
| HBH | 35.0 | 41.9 | 50.1 | 57.6 | 65.1 | 73.5 | 83.0 | 91.3 | 101.5 |

Twenty healthy volunteers were enrolled in a single-dose study using an open label randomized four period crossover design. Eighteen subjects completed the study. Four treatment options were tested in sequence, with a single treatment regimen administered on Study Day 1. A wash out period of at least 5 days was included to separate the dosing days. Each treatment group received each of the four following treatments during the course of the study:

Regimen A: One unit of Formulation F

Regimen B: One unit of Formulation T

Regimen C: One unit of Formulation S

Regimen D: One unit of Vicodin CR tablet

The SR formulations of Regimens A-D were administered under stringent fasting conditions Blood samples were collected from each subject receiving each treatment Regimens for pharmacokinetic sampling at approximate times after administration as follows: 0, 0.25, 0.5, 0.75, 1, 2, 3, 4, 6, 8, 10, 12, 16, 24, 36 and 48 hours.

Blood samples were processed to separate plasma for further analysis, and plasma concentrations of hydrocodone and acetaminophen were determined using a validated HPLC/MS/MS method with quantitation between 0.100 and 100 ng/mL for hydrocodone and 5 and 10,000 ng/mL for acetaminophen. Values for the pharmacokinetic parameters of hydrocodone and acetaminophen were estimated using noncompartmental methods.

The maximum observed plasma concentration ($C_{max}$) and the time to $C_{max}$ (peak time, $T_{max}$) were determined directly from the plasma concentration-time data. The value of the terminal phase elimination rate constant ($\beta$) was obtained from the slope of the least squares linear regression of the logarithms of the plasma concentration versus time data from the terminal log-linear phase of the profile. A minimum of three concentration-time data points was used to determine $\beta$. The terminal phase elimination half-life ($t_{1/2}$) was calculated as $\ln(2)/\beta$. The area under the plasma concentration-time curve (AUC) from time 0 to the time of the last observed concentration ($AUC_t$) was calculated by the linear trapezoidal rule. The AUC was extrapolated to infinite time by dividing the last measured plasma concentration ($C_t$) by $\beta$. Denoting the extrapolated portion of the AUC by $AUC_{ext}$, the AUC from time 0 to infinite time ($AUC_\infty$) was calculated as follows:

$$AUC_\infty = AUC_t + AUC_{ext}$$

The percentage of the contribution of the extrapolated AUC ($AUC_{ext}$) to the overall $AUC_\infty$ was calculated by dividing the $AUC_{ext}$ by the $AUC_\infty$ and multiplying this quotient by 100. The apparent oral clearance value (CL/F, where F is the bioavailability) was calculated by dividing the administered dose by the $AUC_\infty$.

The pharmacokinetic parameter values and summary statistics were computed and tabulated in Tables 14 and 15, respectively. The bioavailability of each test regimen relative to that of the reference regimen was assessed by a two one-sided tests procedure via 90% confidence intervals obtained from the analyses of the natural logarithms of AUC and $C_{max}$. These confidence intervals were obtained by exponentiating the endpoints of confidence intervals for the difference of mean logarithms. The results show subjects receiving one unit of each of the three test formulations prepared according the procedure of Example 3 exhibited a range of sustained release plasma concentrations of hydrocodone and APAP after oral administration at time zero. It is noted that both the in vitro profiles and in vivo absorption profiles of the three test formulations essentially bracket those of the reference for both APAP and HBH, demonstrating the ability to produce a similar in vivo performance by the monoeximic SR design of the present invention. The test Regimens A, B and C were equivalent to the reference Regimen D (Vicodin CR) with respect to AUC for both hydrocodone and APAP because the 90% confidence intervals for evaluating bioequivalence were contained within the 0.80 to 1.25 range. Test Regimens B and C were equivalent to the reference Regimen D with respect to APAP $C_{max}$ and hydrocodone $C_{max}$, respectively, because the 90% confidence intervals for evaluating bioequivalence was contained within the 0.80 to 1.25 range.

TABLE 14

Summary of Pharmacokinetic Parameters of Acetaminophen and Hydrocodone Following Single Dose Oral Administration of Formulations F, T and S of Example 3, and Vicodin CR in Healthy Volunteers (Mean ± SD, n = 18)

| | Pharmacokinetic Parameters Hydrocodone | | | | | |
| --- | --- | --- | --- | --- | --- | --- |
| Regimen | $T_{max}$ (h) | $C_{max}$ (ng/mL) | $AUC_t$ (ng * h/mL) | $AUC_{inf}$ (ng * h/mL) | $t_{1/2}$* (h) | CL/F (L/h) |
| Regimen A (Formulation F) | 4.2 ± 1.2 | 21.3 ± 4.7 | 215 ± 55 | 216 ± 55 | 4.55 ± 0.70 | 44.8 ± 11.7 |
| Regimen B (Formulation T) | 4.7 ± 1.5 | 19.4 ± 3.3 | 222 ± 48 | 223 ± 48 | 4.86 ± 0.63 | 42.5 ± 9.3 |
| Regimen C (Formulation S) | 5.1 ± 1.1 | 16.4 ± 4.8 | 229 ± 64 | 231 ± 64 | 5.30 ± 0.72 | 42.1 ± 11.3 |
| Regimen D (Vicodin CR) | 5.2 ± 3.6 | 14.8 ± 3.3 | 231 ± 52 | 233 ± 52 | 5.27 ± 0.67 | 40.9 ± 9.2 |

| | Acetaminophen | | | | | |
| --- | --- | --- | --- | --- | --- | --- |
| | $T_{max}$ (h) | $C_{max}$ (µg/mL) | $AUC_t$ (µg * h/mL) | $AUC_{inf}$ (µg * h/mL) | $t_{1/2}$* (h) | CL/F (L/h) |
| Regimen A (Formulation F) | 3.5 ± 1.1 | 3.12 ± 0.71 | 27.0 ± 6.9 | 27.3 ± 7.0 | 6.18 ± 1.69 | 19.3 ± 4.3 |
| Regimen B (Formulation T) | 3.4 ± 1.4 | 2.70 ± 0.58 | 27.4 ± 7.3 | 27.7 ± 7.4 | 5.85 ± 1.24 | 19.2 ± 4.6 |
| Regimen C (Formulation S) | 3.9 ± 1.3 | 2.04 ± 0.53 | 28.8 ± 7.8 | 29.1 ± 8.0 | 5.87 ± 1.31 | 18.4 ± 4.8 |
| Regimen D (Vicodin CR) | 1.7 ± 1.5 | 2.51 ± 0.60 | 27.6 ± 7.7 | 28.2 ± 8.1 | 6.33 ± 1.59 | 18.9 ± 4.6 |

*Harmonic mean ± pseudo-standard deviation

TABLE 15

Summary Statistics of Bioavailability Parameters of Acetaminophen and
Hydrocodone Following Single Dose Oral Administration of Formulations F, T and
S of Example 3, and Vicodin CR in Healthy Volunteers (n = 18)

| Regimens Test vs. Reference | Pharmacokinetic Parameter | Central Value* Test | Central Value* Reference | Relative Bioavailability Point Estimate[+] | Relative Bioavailability 90% Confidence Interval |
|---|---|---|---|---|---|
| | | | Hydrocodone | | |
| A (Formulation F) vs. D | $C_{max}$ (ng/mL) | 20.80 | 14.47 | 1.438 | 1.352-1.529 |
| B (Formulation T) vs. D | $C_{max}$ (ng/mL) | 19.06 | 14.47 | 1.317 | 1.239-1.401 |
| C (Formulation S) vs. D | $C_{max}$ (ng/mL) | 15.76 | 14.47 | 1.089 | 1.024-1.158 |
| A (Formulation F) vs. D | $AUC_\infty$ (ng * h/mL) | 208.97 | 227.85 | 0.917 | 0.879-0.957 |
| B (Formulation T) vs. D | $AUC_\infty$ (ng * h/mL) | 218.50 | 227.85 | 0.959 | 0.919-1.000 |
| C (Formulation S) vs. D | $AUC_\infty$ (ng * h/mL) | 222.24 | 227.85 | 0.975 | 0.935-1.017 |
| | | | Acetaminophen | | |
| A (Formulation F) vs. D | $C_{max}$ (ng/mL) | 3051.1 | 2446.3 | 1.247 | 1.168-1.332 |
| B (Formulation T) vs. D | $C_{max}$ (ng/mL) | 2637.0 | 2446.3 | 1.078 | 1.010-1.151 |
| C (Formulation S) vs. D | $C_{max}$ (ng/mL) | 1974.2 | 2446.3 | 0.807 | 0.756-0.862 |
| A (Formulation F) vs. D | $AUC_\infty$ (ng * h/mL) | 26486.4 | 27250.4 | 0.972 | 0.935-1.011 |
| B (Formulation T) vs. D | $AUC_\infty$ (ng * h/mL) | 26898.5 | 27250.4 | 0.987 | 0.949-1.027 |
| C (Formulation S) vs. D | $AUC_\infty$ (ng * h/mL) | 28115.1 | 27250.4 | 1.032 | 0.992-1.073 |

Example 7

Preparation of SRSR Extended Release Dosage Forms Containing Acetaminophen (APAP) and Hydrocodone Bitartrate Hemipentahydrate (HBH) at Lab Scale This example shows the preparation of single unit SRSR matrix dosage forms from single unit monoeximic matrix dosage forms.

Tablets weighing about 800 mg were prepared using wet granulation using a laboratory high shear mixer (Key International Inc.). The same granulations provided for in Table 1 of Example 1 were used to prepare the SRSR system by longitudially compressing combinations of different proportions of the powder blends into bi- or tri-layer cylindrical tablets having a diameter of about 7.32 mm using a hydraulic Carver press. The batch size of each experimental run was about 300 g. Formulations that were investigated to obtain different release profiles are provided in Table 16, below.

Figure 5:
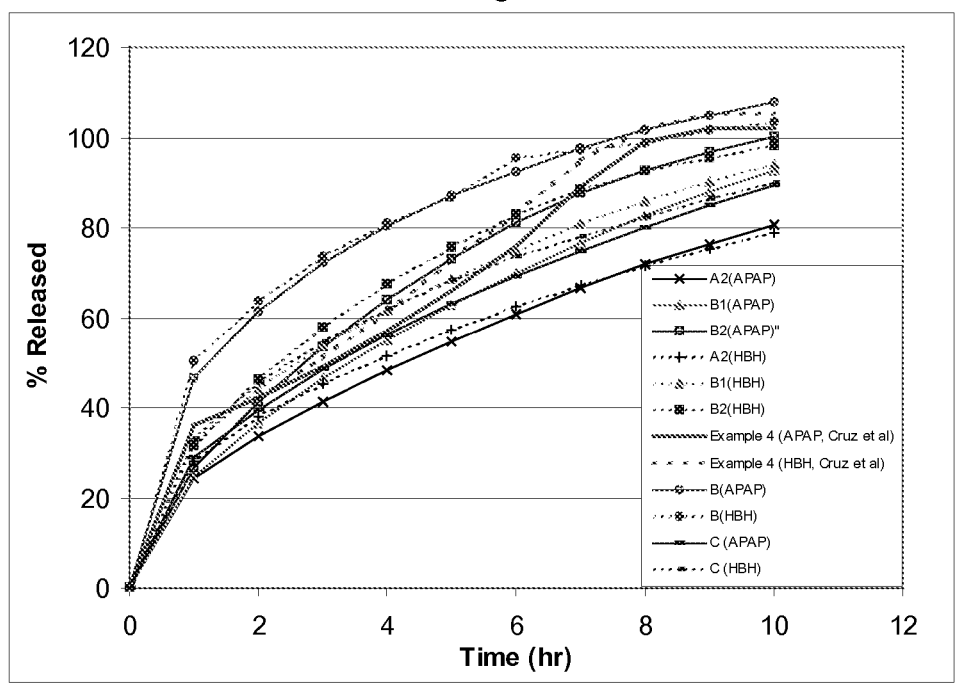
FIG. 5 shows the in vitro drug release of single unit SRSR extended release tablets compared with monoeximic extended release tablets containing APAP and HBH.

Dissolution tests were performed to evaluate the dissolution rates of the single unit SRSR matrix dosage forms using the same method described in Example 1. The results are provided below in Table 17 and FIG. 5. The in vitro studies demonstrated that the SRSR dosage forms of Table 16 produced (1) a range of biphasic extended release profiles with a different percentage (%) of immediate release of APAP and HBH, and (2) similar release rates of APAP and HBH despite the higher solubility of HBH. The reference is the 8-hr osmotic pump system described in Example 4 of Cruz et al. (U.S. Patent Publication No. 20050158382 A1).

TABLE 16

Composition (%) of Single Unit SRSR Layered Tablets Containing
APAP and HBH Prepared Using the Monoeximic Compositions of Table 1

| | Formulation | | | |
|---|---|---|---|---|
| | A1 | A2 | B1 | B2 |
| | Label | | | |
| Configuration | SR1/Mix8 Bilayer | SR1/Mix8/SR1 Trilayer | SR3/Mix8 Bilayer | SR1/Mix8/SR1 Trilayer |
| Layer 1 granules | SR1 (200 mg) | SR1 (100 mg) | SR3 (600 mg) | SR3 (100 mg) |
| Layer 2 granules | Mix8 (600 mg) | Mix8 (600 mg) | Mix8 (200 mg) | Mix8 (600 mg) |
| Layer 3 granules | — | SR1 (100 mg) | — | SR3 (100 mg) |
| Tablet weight | 800 mg | 800 mg | 800 mg | 800 mg |

TABLE 17

In Vitro Dissolution Of APAP and HBH From Single Unit SRSR Matrix Extended Release Tablets

| | Time (hr) | | | | | | | | | |
|---|---|---|---|---|---|---|---|---|---|---|
| | 1 | 2 | 3 | 4 | 5 | 6 | 7 | 8 | 9 | 10 |
| Formulation A1 | | | | | | | | | | |
| APAP | 25.0 | 34.9 | 43.0 | 49.9 | 56.3 | 61.8 | 67.1 | 72.1 | 76.7 | 81.0 |
| HBH | 29.2 | 40.6 | 48.7 | 55.7 | 61.0 | 66.2 | 71.7 | 75.5 | 80.7 | 83.6 |
| Formulation A2 | | | | | | | | | | |
| APAP | 24.2 | 33.6 | 41.3 | 48.3 | 54.7 | 60.8 | 66.5 | 71.8 | 76.2 | 80.7 |
| HBH | 28.1 | 38.1 | 45.3 | 51.5 | 57.1 | 62.6 | 67.1 | 71.4 | 75.2 | 78.9 |
| Formulation B1 | | | | | | | | | | |
| APAP | 24.6 | 36.5 | 46.4 | 55.0 | 62.8 | 69.8 | 76.5 | 82.5 | 87.8 | 92.7 |
| HBH | 32.1 | 44.2 | 53.6 | 61.5 | 68.6 | 74.8 | 80.8 | 85.7 | 90.3 | 94.1 |
| Formulation B2 | | | | | | | | | | |
| APAP | 26.6 | 41.2 | 53.5 | 63.9 | 73.1 | 81.1 | 87.7 | 92.7 | 96.5 | 100.1 |
| HBH | 31.6 | 46.0 | 57.8 | 67.3 | 75.6 | 82.8 | 88.4 | 92.5 | 95.5 | 98.0 |
| Reference (Example 4 of Cruz, et al.) | | | | | | | | | | |
| APAP | 36 | 42 | 49 | 57 | 66 | 76 | 89 | 99 | 102 | 102 |
| HBH | 36 | 42 | 51 | 61 | 73 | 83 | 95 | 102 | 105 | 105 |

Example 8

Preparation of SRSR Extended-Release Dosage Forms Containing APAP and HBH at Pilot Plant Scale This prophetic example shows the preparation of multi-unit SRSR dosage forms based on multi-unit monoeximic matrix dosage forms of Example 3.

The SRSR multi-unit dosage forms can be prepared by utilizing at least two different monoeximic formulations described in Table 5 of Example 3. For example, a SRSR multi-unit dosage form that provides drug release rate within the range of two monoeximic formulations can be prepared by combining tablets of Formulations F and S (monoeximic formulations) of Table 5. More specifically, the release rate can be tailored by encapsulating different ratios of two types of monoeximic small tablets into a single capsule. For example, three dosage forms can be prepared as described below (See, Table 18 below).

Formulation C1 contains three (3) formulation F tablets and one (1) formulation S tablet;

Formulation C2 contains one (1) formulation F tablet and three (3) formulation S tablets; and Formulation C3 contains two (2) formulation F tablets and two (2) formulation S tablets.

Following encapsulation of the tablets, a dissolution test can be performed.

Figure 6:
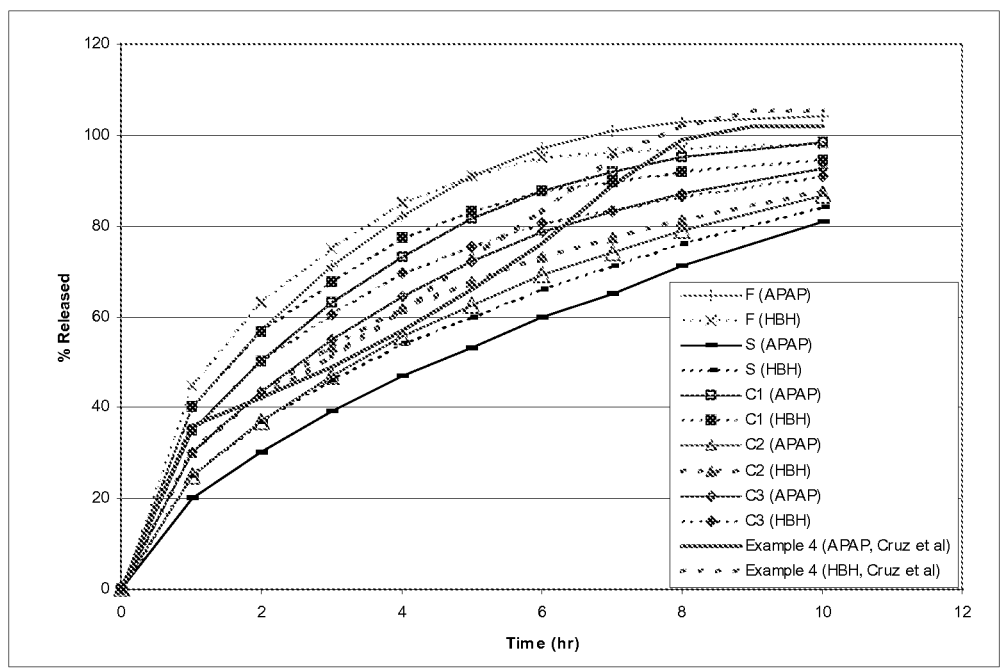
FIG. 6 shows the in vitro drug release of multi-unit SRSR extended release tablets compared with monoeximic extended release tablets containing APAP and HBH.

Because there are no interactions between the drugs being released from each monoeximic formulation, the drug release from each tablet (namely, the APAP and HBH) will be independent of each other. Thus, the drug dissolution profile of APAP or HBH would be a result of the proportional superposition of the individual APAP and HB profiles if such a study were performed. The results provided in Table 19 below show that the dissolution profiles of APAP and HBH can be tailored using different ratios of Formulation F and S to produce a range of biphasic extended release profiles with a range of immediate release and extended release profiles that bracket the release profile of the reference, namely, the 8-hr osmotic pump system described in Example 4 of Cruz et al. (U.S. Patent Publication No. 20050158382 A1). The data compared with the reference is also shown in FIG. 6.

TABLE 18

Composition (%) of Multi-Unit SRSR Extended Release Dosage Forms Containing APAP and HBH Prepared Using Tablets of Table 5.

| | Formulation | | |
|---|---|---|---|
| | C1 | C2 | C3 |
| | Label | | |
| | F/S(0.25/0.75) | F/S(0.75/0.25) | F/S(0.5/0.5) |
| Number of Formulation F tablet | 1 | 3 | 2 |
| Number of Formulation S tablet | 3 | 1 | 2 |

TABLE 19

In Vitro Dissolution of APAP And HBH From Multi-Unit Monoeximic Matrix and SRSR Extended Release Tablets Based On Data of Monoeximic Matrix in Table 6

| | Time (hr) | | | | | | | | |
|---|---|---|---|---|---|---|---|---|---|
| | 1 | 2 | 3 | 4 | 5 | 6 | 7 | 8 | 10 |
| Formulation C1* (F/S: 0.25/0.75) | | | | | | | | | |
| APAP | 35 | 50 | 63 | 73 | 82 | 88 | 92 | 95 | 98 |
| HBH | 40 | 57 | 68 | 77 | 83 | 88 | 90 | 92 | 95 |
| Formulation C2* (F/S: 0.75/0.25) | | | | | | | | | |
| APAP | 25 | 37 | 47 | 56 | 63 | 69 | 74 | 79 | 87 |
| HBH | 30 | 44 | 53 | 62 | 68 | 73 | 77 | 81 | 88 |

TABLE 19-continued

In Vitro Dissolution of APAP And HBH From Multi-Unit
Monoeximic Matrix and SRSR Extended Release Tablets
Based On Data of Monoeximic Matrix in Table 6

| | Time (hr) | | | | | | | | |
|---|---|---|---|---|---|---|---|---|---|
| | 1 | 2 | 3 | 4 | 5 | 6 | 7 | 8 | 10 |
| Formulation C3* (F/S: 0.5/0.5) | | | | | | | | | |
| APAP | 30 | 44 | 55 | 65 | 72 | 79 | 83 | 87 | 93 |
| HBH | 35 | 50 | 61 | 70 | 76 | 81 | 84 | 87 | 91 |
| Reference (Example 4 of Cruz, et al.) | | | | | | | | | |
| APAP | 36 | 42 | 49 | 57 | 66 | 76 | 89 | 99 | 102 |
| HBH | 36 | 42 | 51 | 61 | 73 | 83 | 95 | 102 | 105 |

*Data calculated by the proportional superposition of data from formulations F and S at different ratios

Example 9

Preparation of SRSR Extended-Release Dosage Forms Containing APAP and HBH at Lab Scale This partially prophetic example shows the preparation of multi-unit SRSR reservoir and reservoir-matrix dosage forms based on multi-unit monoeximic reservoir and matrix dosage forms.

(1) Multi-Unit Monoeximic Reservoir Dosage Forms

Tablets weighing 200 mg were prepared using wet granulation. Specifically, APAP dense powder was dry mixed with HBH, lactose, SSG (for R2) and SDS for 1.0 minutes (150 rpm) followed by granulation with an Eudragit® L-30D aqueous dispersion at low speed (200 rpm) for approximately 1.5 minutes in a laboratory high shear mixer (Key International Inc.). The wet granules were then dried in an oven at 50° C. overnight and passed through a 20-mesh screen. The granulation was blended with hydroxylpropyl cellulose (HPC) and silicon dioxide for 3.0 minutes and then with magnesium stearate for an additional 2.0 minutes at 25 rpm in a V-blender. The powder blend was subsequently compressed into tablets using a hydraulic Carver press. The diameter of the tablets is about 4.40 mm. The granulation batch size was about 150 g.

To modify the release of both APAP and HBH, the tablets were coated in a laboratory coating pan having a diameter of 20.3 cm. The membrane coating solution was prepared by dissolving ethylcellulose (EC), HPC and triethyl citrate (TEC) using acetone as a solvent. The tablets were loaded in the coating pan rotating at 60 rpm and sprayed with the coating solution with a solid content of 18% using a air paint spray-gun until the tablet weight gain reached 5%. The final dosage form was obtained by filling 4 coated tablets into a Size 00 capsule for dissolution testing. Different formulations were studied to obtain different release rates. Example formulations are provided in Table 22, below.

(2) Multi-Unit SRSR Reservoir Dosage Forms

The SRSR multi-unit reservoir dosage forms can be prepared by utilizing two different monoeximic reservoir formulations as described below in Table 20. For example, a SRSR multi-unit dosage form that provides a drug release rate within the range of the two monoeximic formulations can be prepared by combining tablets of Formulations R1 and R2 of Table 20. More specifically, the release rate can be tailored by encapsulating different ratios of the two types of monoeximic small tablets into a single capsule. For example, two dosage forms can be prepared as described below (See, Table 21 below).

Formulation C4 contains three (3) Formulation R1 tablets and one (1) Formulation R2 tablet; and Formulation C5 contains two (2) Formulation R1 tablets and two (2) Formulation R2 tablets.

Following encapsulation of the tablets, a dissolution test can be performed. Because there are no interactions between the drugs being released from each monoeximic formulation, the drug release from each tablet (namely, the APAP and HBH) will be independent of each other. Thus, the drug dissolution profile of APAP or HBH would be a result of the proportional superposition of the individual APAP and HB profiles if such a study were performed.

(3) Multi-Unit SRSR Reservoir-Matrix Dosage Forms

SRSR multi-unit reservoir-matrix dosage forms can be prepared utilizing at least one monoeximic reservoir form described below in Table 20 and one monoeximic matrix formulation described above in Table 5 of Example 3. For example, the SRSR multi-unit dosage form that provides drug release rate within the range of the two monoeximic formulations can be prepared by combining tablets of Formulations R1 or R2 of Table 20 and Formulations F or S of Table 5. More specifically, the release rate can be tailored by encapsulating different ratios of the two monoeximic small tablets into a single capsule. For example, two dosage forms can be prepared as described below (See, Table 21 below).

Formulation C6 contains three (3) Formulation R1 tablets and one (1) Formulation F tablet;

Formulation C7 contains two (2) Formulation R1 tablets and two (2) Formulation S tablets.

Following encapsulation of the tablets, a dissolution test can be performed.

Because there are no interactions between the drugs being released from each monoeximic formulation, the drug release from each tablet (namely, the APAP and HBH) will be independent of each other. Thus, the drug dissolution profile of APAP or HBH would be a result of the proportional superposition of the individual APAP and HB profiles if such a study were performed.

(4) In Vitro Dissolution Rate

Figure 7:
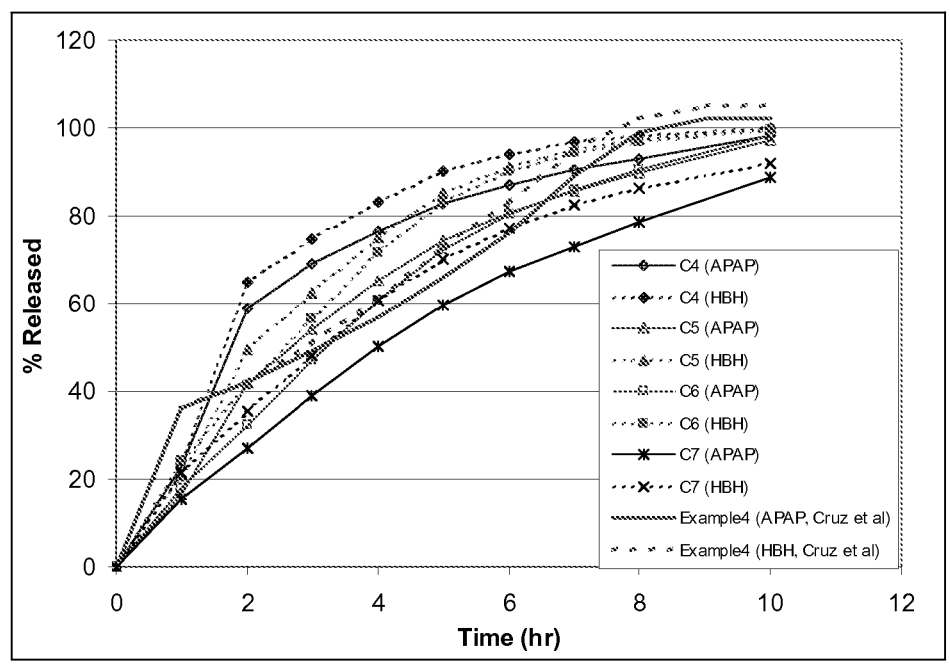
FIG. 7 shows the in vitro drug release of multi-unit SRSR extended release tablets containing APAP and HBH

Dissolution tests were performed to evaluate the dissolution rates of the monoeximic dosage forms of Table 20 using the same method described in Example 1. The results provided in Table 22 below show that the dissolution profiles can be tailored using different ratios of monoeximic reservoir and/or matrix formulations to produce a range of extended release profiles that bracket the overall release profile of the reference, namely, the 8-hr osmotic pump system described in Example 4 of Cruz et al. (U.S. Patent Publication No. 20050158382 A1). The data compared with the reference is also shown in FIG. 7.

TABLE 20

Composition (%) of Multi-Unit Monoeximic Reservoir Extended Release Tablets Containing APAP and HBH

| | Formulation | |
|---|---|---|
| | R1 | R2 |
| Core tablet | | |
| APAP Dense Powder, | 62.5 | 62.5 |
| HBH | 1.9 | 1.9 |

TABLE 20-continued

Composition (%) of Multi-Unit Monoeximic Reservoir Extended Release Tablets Containing APAP and HBH

| | Formulation | |
|---|---|---|
| | R1 | R2 |
| Eudragit L-30D-55 -dry weight- | 4.5 | 4.5 |
| Lactose monohydrate | 25.1 | 24.1 |
| HPC, Klucel EXF | 2.0 | 2.0 |
| Sodium Starch Glycolate (SSG) | — | 1.0 |
| Sodium Dodecyl sulphate (SDS) | 2.0 | 2.0 |
| Silicon dioxide | 1.0 | 1.0 |
| Magnesium Stearate | 1.0 | 1.0 |
| Tablet weight (mg) | 200 mg | |
| Membrane Coating | | |
| Ethylcellulose | 38.9 | 38.9 |
| HPC, Klucel EXF | 44.4 | 44.4 |
| Triethyl citrate | 16.7 | 16.7 |
| Coating Weight | 10 mg (5% weight gain) | |

TABLE 21

Composition (%) of Multi-Unit SRSR Reservoir and Reservoir-Matrix Extended Release Dosage Forms Containing APAP and HBH Prepared Using Tablets of Tables 16 And 22

| | Formulation | | | |
|---|---|---|---|---|
| | C4 | C5 | C6 | C7 |
| Label | R1/R2 (0.5/0.5) | R1/R2 (0.75/0.25) | F/R1 (0.25/0.75) | S/R1 (0.5/0.5) |
| Type | SRSR reservoir | | SRSR reservoir-matrix | |
| Number of Formulation R1 tablet | 2 | 3 | 3 | 2 |
| Number of Formulation R2 tablet | 2 | 1 | — | — |
| Number of Formulation F tablet | — | — | 1 | — |
| Number of Formulation S tablet | — | — | — | 2 |

TABLE 22

In Vitro Dissolution of APAP And HBH From Multi-Unit Monoeximic Reservoir and SRSR Extended Release Dosage Forms

| | Time (hr) | | | | | | | | |
|---|---|---|---|---|---|---|---|---|---|
| | 1 | 2 | 3 | 4 | 5 | 6 | 7 | 8 | 10 |
| Monoeximic reservoir | | | | | | | | | |
| Formulation R1 | | | | | | | | | |
| APAP | 11 | 24 | 39 | 54 | 66 | 75 | 81 | 87 | 96 |
| HBH | 17 | 34 | 50 | 67 | 81 | 89 | 94 | 97 | 100 |
| Formulation R2 | | | | | | | | | |
| APAP | 35 | 94 | 99 | 99 | 99 | 100 | 100 | 100 | 100 |
| HBH | 31 | 96 | 99 | 99 | 100 | 99 | 100 | 100 | 100 |
| SRSR reservoir | | | | | | | | | |
| Formulation C4* (R1/R2 = 0.5/0.5) | | | | | | | | | |
| APAP | 23 | 59 | 69 | 76 | 83 | 87 | 90 | 93 | 98 |
| HBH | 24 | 65 | 75 | 83 | 90 | 94 | 97 | 98 | 100 |
| Formulation C5* (R1/R2 = 0.75/0.25) | | | | | | | | | |
| APAP | 17 | 42 | 54 | 65 | 75 | 81 | 86 | 90 | 97 |
| HBH | 21 | 50 | 62 | 75 | 85 | 91 | 95 | 98 | 100 |
| SRSR reservoir-matrix | | | | | | | | | |
| Formulation C6* (F/R1 = 0.25/0.75) | | | | | | | | | |
| APAP | 18 | 32 | 47 | 61 | 72 | 80 | 86 | 91 | 98 |
| HBH | 24 | 41 | 56 | 72 | 83 | 90 | 94 | 97 | 100 |
| Formulation C7* (S/R1 = 0.5/0.5) | | | | | | | | | |
| APAP | 15 | 27 | 39 | 50 | 60 | 67 | 73 | 79 | 89 |
| HBH | 21 | 36 | 48 | 61 | 70 | 77 | 82 | 86 | 92 |
| Reference (Example 4 of Cruz, et al.) | | | | | | | | | |
| APAP | 36 | 42 | 49 | 57 | 66 | 76 | 89 | 99 | 102 |
| HBH | 36 | 42 | 51 | 61 | 73 | 83 | 95 | 102 | 105 |

*Data calculated by proportional superposition of data from formulations R1, R2, F and S at different ratios The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

What is claimed is:

1. A pharmaceutical composition comprising at least two sustained release subunits:
   a first sustained release subunit that comprises acetaminophen and hydrocodone or an equivalent amount of another acceptable salt or free base of hydrocodone thereof;
   a second sustained release subunit that comprises acetaminophen and hydrocodone or an equivalent amount of another acceptable salt or free base of hydrocodone thereof;
   wherein each of the sustained release subunits are in a monoeximic dosage form selected from the group consisting of an osmotic system and a matrix system,
   wherein each monoexemic osmotic system contains only one membrane to control the rate of drug release, and
   wherein the sustained release subunits release the drugs contained therein over a period of longer than two hours.

2. The pharmaceutical composition of claim 1, wherein the composition contains acetaminophen between about 20 and about 100 times by weight of hydrocodone bitartrate or an equivalent amount of another acceptable salt or free base of hydrocodone thereof.

3. The pharmaceutical composition of claim 1, wherein the first subunit and the second subunit each contain a single rate controlling mechanism.

4. The pharmaceutical composition of claim 3, wherein the single rate controlling mechanism comprises at least one pharmaceutically acceptable hydrophobic rate controlling material, a pharmaceutically acceptable hydrophilic rate controlling material, a non-polymer rate controlling material or any combinations thereof.

5. The pharmaceutical composition of claim 1, wherein the first and second subunit each comprise a monoeximic dosage form.

6. The pharmaceutical composition of claim 5, wherein the first and second subunits comprise the same type of monoeximic dosage forms or different types of monoeximic dosage forms.

7. The pharmaceutical composition of claim 6, wherein each of the monoeximic dosage forms comprises a matrix system.

8. The pharmaceutical composition of claim 6, wherein each of the monoeximic dosage forms comprises an osmotic system.

9. The pharmaceutical composition of claim 6, wherein one of the monoeximic dosage forms comprises a matrix system and the other monoeximic dosage forms comprises an osmotic system.

10. The pharmaceutical composition of claim 1, wherein the composition is capable of reducing pain intensity in a patient within about 1 hour.

11. The pharmaceutical composition of claim 10, wherein the composition releases at least 90% of the hydrocodone and acetaminophen in vitro within 12 hours.

12. The pharmaceutical composition of claim 10, wherein the composition releases at least 90% of the hydrocodone and acetaminophen in vitro within about 8 hours.

13. The pharmaceutical composition of claim 1, wherein the dosage form is adapted to release about 19% to 49% of the hydrocodone and acetaminophen in vitro within 0.75 hours.

14. The pharmaceutical composition of claim 13, wherein the dosage form releases at least 90% of the hydrocodone and acetaminophen within 12 hours.

15. The pharmaceutical composition of claim 13, wherein the dosage releases at least 90% of the hydrocodone and acetaminophen within about 8 hours.

16. The pharmaceutical composition of claim 1, wherein the dosage form comprises about 500 mg of acetaminophen and about 15 mg of hydrocodone bitartrate.

17. The pharmaceutical composition of claim 1, wherein the human in which the AUC and Cmax for both hydrocodone and acetaminophen is measured is a non-poor CYP2D6 metabolizer, and wherein the dosage form produces a Cmax for hydromorphone in the human of between about 0.12 ng/ml and about 0.35 ng/ml after a single dose of 30 mg of hydrocodone bitartrate.

18. The pharmaceutical composition of claim 1, wherein the plasma concentration for hydrocodone 12 hours after a single 30 mg dose of hydrocodone bitartrate is between about 11.0 ng/ml and about 27.4 ng/ml.

19. The pharmaceutical composition of claim 1, wherein when a single 1000 mg dose of acetaminophen is administered to the human, the plasma concentration for acetaminophen 12 hours after administration is between about 0.7 µg/ml and about 2.5 µg/ml.

20. The pharmaceutical composition of claim 1, wherein when a single 1000 mg dose of acetaminophen is administered to the human, the plasma concentration for acetaminophen 12 hours after administration is between about 0.7 µg/ml and about 2.5 µg/ml.

21. The pharmaceutical composition of claim 1, wherein after a single dose of 30 mg of hydrocodone bitartrate, the plasma concentration profile exhibits a width at half height for hydrocodone of between about 6.4 hours and about 19.6 hours.

22. The pharmaceutical composition of claim 1, wherein after a single dose of 30 mg of hydrocodone bitartrate, the plasma concentration profile exhibits a width at half height for hydrocodone of between about 8.4 hours and about 19.6 hours.

23. The sustained pharmaceutical composition of claim 1, wherein after a single does of 1000 mg of acetaminophen, the plasma concentration profile exhibits a width at half height for acetaminophen of between about 0.8 hours and about 12.3 hours.

* * * * *